United States Patent [19]

Lok et al.

[11] Patent Number: 4,882,038

[45] Date of Patent: * Nov. 21, 1989

[54] PROCESS FOR THE USE OF MAGNESIUM-ALUMINUM-PHOSPHORUS-SILICON-OXIDE MOLECULAR SIEVE COMPOSITIONS

[75] Inventors: Brent M. T. Lok, New City; Lawrence D. Vail, New Rochelle; Edith M. Flanigen, White Plains, all of N.Y.

[73] Assignee: UOP, Des Plaines, Ill.

[*] Notice: The portion of the term of this patent subsequent to Apr. 26, 2005 has been disclaimed.

[21] Appl. No.: 155,696

[22] Filed: Feb. 16, 1988

Related U.S. Application Data

[62] Division of Ser. No. 600,180, Apr. 18, 1984, Pat. No. 4,758,419.

[51] Int. Cl.$^4$ ............................................. C10G 47/02
[52] U.S. Cl. ................................. 208/111; 208/120; 208/136; 585/266; 585/275; 585/415; 585/481; 585/475; 585/514; 585/527; 585/533; 585/667; 585/666; 585/731; 585/740
[58] Field of Search ................ 208/111, 120, 136; 585/266, 275, 415, 481, 475, 514, 527, 533, 667, 666, 731, 740

[56] References Cited

U.S. PATENT DOCUMENTS

| | | | |
|---|---|---|---|
| 3,941,871 | 5/1976 | Dwyer et al. | 423/326 |
| 4,061,724 | 12/1977 | Grose et al. | 423/335 |
| 4,310,440 | 1/1982 | Wilson et al. | 252/435 |
| 4,420,467 | 12/1983 | Whittam | 423/328 |
| 4,440,871 | 4/1984 | Lok et al. | 502/214 |
| 4,486,397 | 12/1984 | Eshraghi et al. | 423/306 |
| 4,500,651 | 2/1985 | Lok et al. | 502/208 |
| 4,554,143 | 11/1985 | Messina et al. | 423/306 |
| 4,567,029 | 1/1986 | Wilson et al. | 423/306 |
| 4,612,406 | 9/1986 | Long et al. | 585/415 |
| 4,740,650 | 4/1988 | Pellet et al. | 585/481 |
| 4,758,419 | 7/1988 | Lok et al. | 423/306 |

FOREIGN PATENT DOCUMENTS

| | | |
|---|---|---|
| 885436 | 11/1971 | Canada. |
| 0054364 | 6/1982 | European Pat. Off.. |
| 0055046 | 6/1982 | European Pat. Off.. |
| 0055529 | 7/1982 | European Pat. Off.. |
| 0059059 | 9/1982 | European Pat. Off.. |
| 984502 | 2/1965 | United Kingdom. |

OTHER PUBLICATIONS

Schmitz-DuMont, Zeitschrift fur Anorganische und Allgemeine Chemie, 302, 121-135 (1959).

*Primary Examiner*—Asok Pal
*Attorney, Agent, or Firm*—Thomas K. McBride; Eugene I. Snyder; Frank S. Molinaro

[57] ABSTRACT

Crystalline molecular sieves having a three-dimensional microporous framework structures of $MgO_2$, $AlO_2$, $SiO_2$ and $PO_2$ tetrahedral units are disclosed. These molecular sieves have an empirical chemical composition on an anhydrous basis expressed by the formula:

$$mR: (Mg_wAl_xP_ySi_z)O_2$$

wherein "R" represents at least one organic templating agent present in the intracrystalline pore system; "m" represents the molar amount of "R" present per mole of $(Mg_wAl_xP_ySi_z)O_2$; and "w", "x", "y" and "z" represent the mole fractions of magnesium, aluminum, phosphorus and silicon, respectively, present as tetrahedral oxides. Their use as adsorbents, catalysts, etc. is disclosed.

5 Claims, 3 Drawing Sheets

PROCESS FOR THE USE OF MAGNESIUM-ALUMINUM-PHOSPHORUS-SILICON-OXIDE MOLECULAR SIEVE COMPOSITIONS

This application is a divisional application of U.S. application Ser. No. 600,180 filed Apr. 13, 1984, now U.S. Pat. No. 4,758,419.

FIELD OF THE INVENTION

The instant invention relates to processes for the use of a novel class of crystalline microporous molecular sieves, as adsorbents and catalysts. The invention relates to novel magnesium-aluminum-phosphorus-silicon-oxide molecular sieves having magnesium, aluminum, phosphorus and silicon in the form of framework tetrahedral oxides. These compositions may be prepared hydrothermally from gels containing reactive compounds of magnesium, aluminum, phosphorus and silicon capable of forming framework tetrahedral oxides, and preferably at least one organic templating agent which functions in part to determine the course of the crystallization mechanism and the structure of the crystalline product.

BACKGROUND OF THE INVENTION

Molecular sieves of the crystalline aluminosilicate zeolite type are well known in the art and now comprise over 150 species of both naturally occurring and synthetic compositions. In general the crystalline zeolites are formed from corner-sharing $AlO_2$ and $SiO_2$ tetrahedra and are characterized by having pore openings of uniform dimensions, having a significant ion-exchange capacity and being capable of reversibly desorbing an adsorbed phase which is dispersed throughout the internal voids of the crystal without displacing any atoms which make up the permanent crystal structure.

Other crystalline microporous compositions which are not zeolitic, i.e. do not contain $AlO_2$ tetrahedra as essential framework constituents, but which exhibit the ion-exchange and/or adsorption characteristics of the zeolites are also known. Metal organosilicates which are said to possess ion-exchange properties, have uniform pores and are capable of reversibly adsorbing molecules having molecular diameters of about 6 Å or less, are reported in U.S. Pat. No. 3,941,871 issued Mar. 2, 1976 to Dwyer et al. A pure silica polymorph, silicalite, having molecular sieving properties and a neutral framework containing neither cations nor cation sites is disclosed in U.S. Pat. No. 4,061,724 issued Dec. 6, 1977 to R. W. Grose et al.

A recently reported class of microporous compositions and the first framework oxide molecular sieves synthesized without silica, are the crystalline aluminophosphate compositions disclosed in U.S. Pat. No. 4,310,440 issued Jan. 12, 1982 to Wilson et al. These materials are formed from $AlO_2$ and $PO_2$ tetrahedra and have electrovalently neutral frameworks as in the case of silica polymorphs. Unlike the silica molecular sieve, silicalite, which is hydrophobic due to the absence of extra-structural cations, the aluminophosphate molecular sieves are moderately hydrophilic, apparently due to the difference in electronegativity between aluminum and phosphorus. Their intracrystalline pore volumes and pore diameters are comparable to those known for zeolites and silica molecular sieves.

In copending and commonly assigned application Ser. No. 400,438, filed July 26, 1982 (now U.S. Pat. No. 4,440,871), there is described a novel class of silicon-substituted aluminophosphates which are both microporous and crystalline. The materials have a three dimensions crystal framework of $PO_2^+$, $AlO_2^-$ and $SiO_2$ tetrahedral unites and, exclusive of any alkali metal or calcium which may optionally be present, an as-synthesized empirical chemical composition on an anhydrous basis of:

$$mR:(Si_xAl_yP_z)O_2$$

wherein "R" represents at least one organic templating agent present in the intracrystalline pore system: "m" represents the moles of "R" present per mole of $(Si_xAl_yP_z)O_2$ and has a value of from zero to 0.3; the maximum value in each case depending upon the molecular dimensions of the templating agent and the available void volume of the pore system of the particular silicoaluminophosphate species involved; and "x", "y", and "z" represent the mole fractions of silicon, aluminum and phosphorus, respectively, present as tetrahedral oxides. The minimum value for each of "x", "y", and "z" is 0.01 and preferably 0.02. The maximum value for "x" is 0.98; for "y" is 0.60; and for "z" is 0.52. These silicoaluminophosphates exhibit several physical and chemical properties which are characteristic of aluminosilicate zeolites and aluminophosphates.

In copending and commonly assigned U.S. Ser. No. 480,738, filed Mar. 31, 1983 (now U.S. Pat. No. 4,500,651), there is disclosed a novel class of crystalline titanium-containing molecular sieves having a unit empirical formula

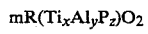

$$mR(Ti_xAl_yP_z)O_2$$

wherein "R" represents at least organic templating agent present in the intracrystalline pore system; "m" represents the moles of "R" present per mole of $(Ti_xAl_yP_z)O_2$ and has a value of between zero and about 5.0; and "x", "y" and "z" represent the mole fractions of titanium, aluminum and phosphorus, respectively, present as tetrahedral oxides.

In copending and commonly assigned application U.S. Ser. No. 514,334, filed July 15, 1983, (now U.S. Pat. No. 4,567,029) there is described a novel class of crystalline metal aluminophosphates having three-dimensional microporous framework structures of $MO_2$, $AlO_2$ and $PO_2$ tetrahedral units and having an empirical chemical composition on an anhydrous basis expressed by the formula:

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3; "M" represents at least one metal of the group magnesium, manganese, zinc and cobalt; and "x", "y" and "z" represent the mole fractions of "M", aluminum and phosphorus, respectively, present as tetrahedral oxides.

In copending and commonly assigned U.S. Ser. No. 514,335, filed July 15, 1983, (now U.S. Pat. No. 4,683,217) there is described a novel class of crystalline ferroaluminophosphates having three-dimensional microporous framework structures of $FeO_2$, $AlO_2$ and PO$_2$ tetrahedral units and having an empirical chemical composition on an anhydrous basis expressed by the formula:

$$mR:(Fe_xAl_yP_z)O_2$$

wherein "R" represents at least one organic templating agent present in the intracrystalline pore system; "m" represents the moles of "R" present per mole of (Fe$_x$Al$_y$P$_z$)O$_2$ and has a value of from zero to 0.3; and "x", "y" and "z" represent the mole fractions of iron, aluminum and phosphorus, respectively, present as tetrahedral oxides.

The instant invention relates to new molecular sieves having framework tetrahedral oxides of MgO$_2^{-2}$, AlO$_2^-$, PO$_2^+$ and SiO$_2$.

SUMMARY OF THE INVENTION

The instant invention relates to a new class of crystalline molecular sieves having a three-dimensional microporous framework structure of MgO$_2^{-2}$, AlO$_2^-$, PO$_2^+$ and SiO$_2$ tetrahedral oxide units. These new magnesium-aluminum-phosphorus-silicon molecular sieves exhibit ion-exchange, adsorption and catalytic properties and, accordingly, find wide use as adsorbents and catalysts. The members of this novel class of compositions have crystal framework structures of MgO$_2^{-2}$, AlO$_2^-$, PO$_2^+$ and SiO$_2$ tetrahedral units and have an empirical chemical composition on an anhydrous basis expressed by the formula:

$$mR:(Mg_wAl_xP_ySi_z)O_2$$

wherein "R" represents at least one organic templating agent present in the intracrystalline pore system; "m" represents the molar amount of "R" present per mole of (Mg$_w$Al$_x$P$_y$Si$_z$)O$_2$ and has a value from zero to about 0.3; and "w", "x", "y" and "z" represent the mole fractions of magnesium, aluminum, phosphorus and silicon, respectively, present as tetrahedral oxides.

The instant molecular sieve compositions are characterized in several ways as distinct from heretofore known molecular sieves, including the aforementioned ternary compositions. The instant molecular sieves are characterized by enhanced thermal stability of certain species and by the existence of species heretofore unknown for binary and ternary molecular sieves.

The molecular sieves of the instant invention will be generally referred to by the acronym "MgAPSO" to designate a framework having MgO$_2^{-2}$, AlO$_2^-$, PO$_2^+$ and SiO$_2$ tetrahedral units. Actual class members will be identified as structural species by assigning a number to the species and, accordingly, are identified as "MgAPSO-i" wherein "i" is an integer. This designation is an arbitrary one and is not intended to denote structural relationship to another material(s) which may also be characterized by a numbering system.

DETAILED DESCRIPTION OF THE INVENTION

The instant invention relates to a new class of crystalline molecular sieves having three-dimensional microporous crystal framework structures of MgO$_2^{-2}$, AlO$_2^-$, PO$_2^+$ and SiO$_2$ tetrahedral oxide units. These new molecular sieves exhibit ion-exchange, adsorption and catalytic properties and, accordingly, find wide use as adsorbents and catalysts.

Figure 1:
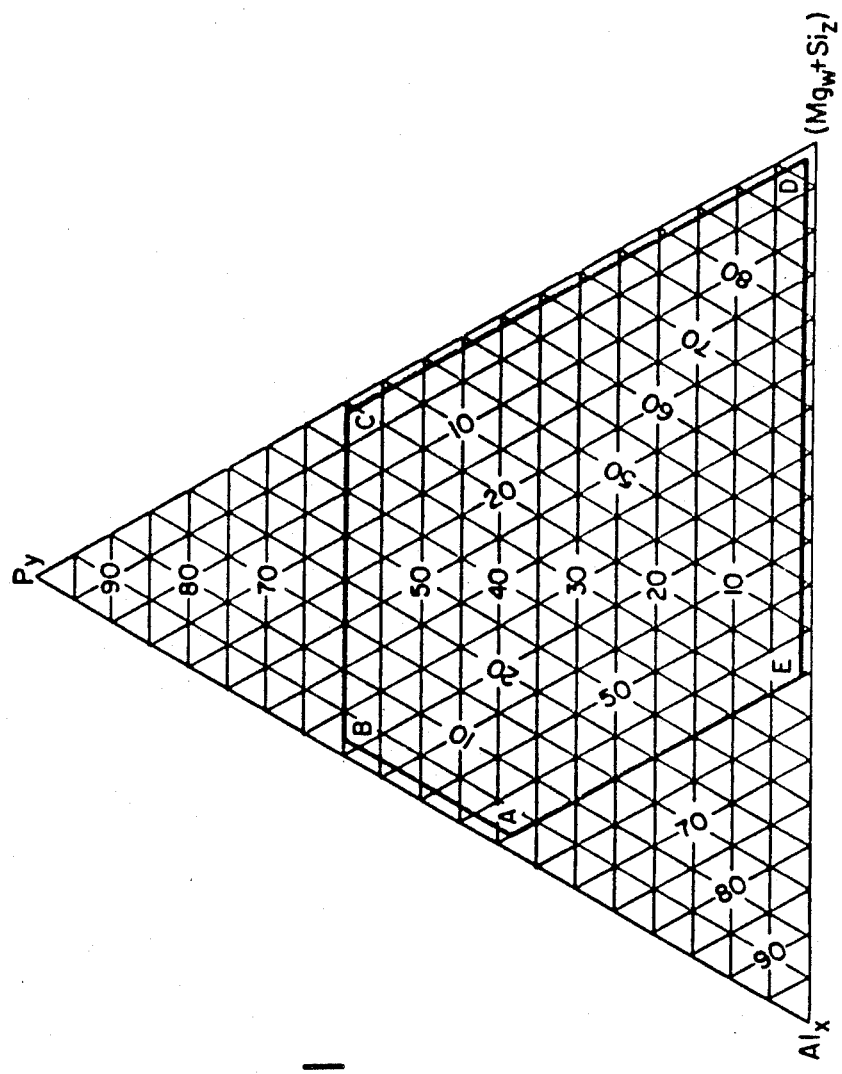
FIG. 1 is a ternary diagram wherein parameters relating to the instant compositions are set forth as mole fractions.

The molecular sieves of the instant invention have three-dimensional microporous framework structures of MgO$_2^{-2}$, AlO$_2^-$, PO$_2^+$ and SiO$_2$ tetrahedral oxide units and have an empirical chemical composition on an anhydrous basis expressed by the formula:

$$mR:(Mg_wAl_xP_ySi_z)O_2$$

wherein "R" represents at least one organic templating agent present in the intracrystalline pore system; "m" represents the molar amount of "R" present per mole of (Mg$_w$Al$_x$P$_y$Si$_z$)O$_2$ and has a value from zero (0) to about 0.3; and "w", "x", "y" and "z" represent the mole fractions of magnesium, aluminum, phosphorus and silicon, respectively, present as tetrahedral oxides and each preferably has a value of at least 0.01. The mole fractions "w", "x", "y" and "z" are generally defined as being within the pentagonal compositional area defined by points A, B, C, D and E of the ternary diagram of FIG. 1. Points A, B, C, D and E of FIG. 1 have the following values for "w", "x", "y" and "z":

|       | Mole Fraction |      |         |
|-------|---------------|------|---------|
| Point | x             | y    | (z + w) |
| A     | 0.60          | 0.38 | 0.02    |
| B     | 0.39          | 0.59 | 0.02    |
| C     | 0.01          | 0.60 | 0.39    |
| D     | 0.01          | 0.01 | 0.98    |
| E     | 0.60          | 0.01 | 0.39    |

Figure 2:
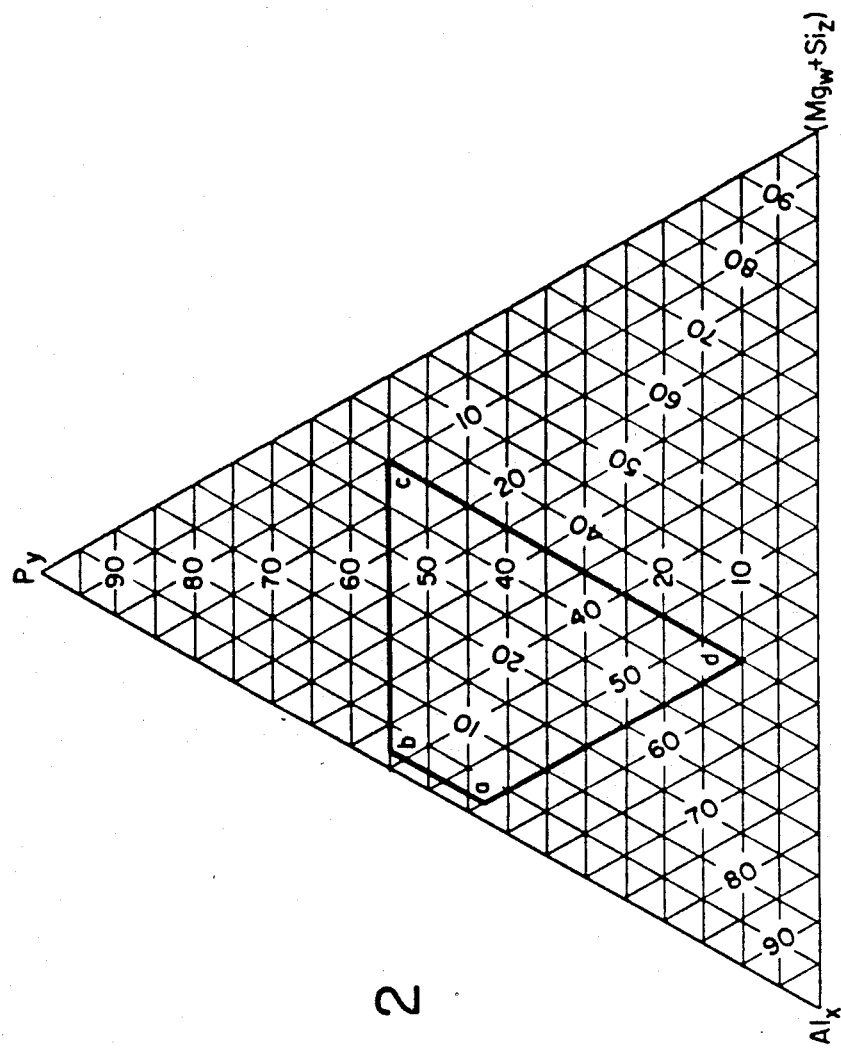
FIG. 2 is a ternary diagram wherein parameters relating to preferred compositions are set forth as mole fractions.

In a preferred subclass of the MgAPSO molecular sieves the values "w", "x", "y" and "z" in the above formula are within the tetragonal compositional area defined by the points a, b, c and d of the ternary diagram of FIG. 2, said points a, b, c and d representing the following values for "w", "x", "y" and "z":

|       | Mole Fraction |      |         |
|-------|---------------|------|---------|
| Point | x             | y    | (z + w) |
| a     | 0.55          | 0.43 | 0.02    |
| b     | 0.43          | 0.55 | 0.02    |
| c     | 0.10          | 0.55 | 0.35    |
| d     | 0.55          | 0.10 | 0.35    |

The MgAPSOs of this invention are useful as adsorbents, catalysts, ion-exchangers, and the like in much the same fashion as aluminosilicates have been employed heretofore, although their chemical and physical properties are not necessarily similar to those observed for aluminosilicates.

MgAPSO compositions are generally synthesized by hydrothermal crystallization for an effective time at effective pressures and temperatures from a reaction mixture containing reactive sources of magnesium, silicon, aluminum and phosphorus, an organic templating, i.e., structure-directing, agent, preferably a compound of an element or Group VA of the Periodic Table, and may be an alkali or other metal. The reaction mixture is generally placed in a sealed pressure vessel, preferably lined with an inert plastic material such as polytetrafluoroethylene and heated, preferably under autogenous pressure at a temperature between 50° C. and 250° C., and preferably between 100° C. and 200° C. until crystals of the MgAPSO product are obtained, usually a period of from several hours to several weeks. Generally, the crystallization period will be from about 2 hours to about 30 days with it typically being from about 4 hours to about 20 days for obtaining MgAPSO crystals. The product is recovered by any convenient method such as centrifugation or filtration.

In synthesizing the MgAPSO compositions of the instant invention, it is preferred to employ reaction mixture compositions expressed in terms of the molar ratios as follows:

$aR:(Mg_rAl_sP_tSi_u)O_2:bH_2O$ wherein "R" is an organic templating agent; "a" is the amount of organic templating agent "R" and can have a value within the range of from zero (0) to about 6 and is more preferably an effective amount greater than zero to about 6; "b" has a value of from zero (0) to about 500, preferably between about 2 and about 300; and "r", "s", "t" and "u" represent the mole fractions of magnesium, aluminum, phosphorus and silicon, respectively, and each has a value of at least 0.01.

Figure 3:
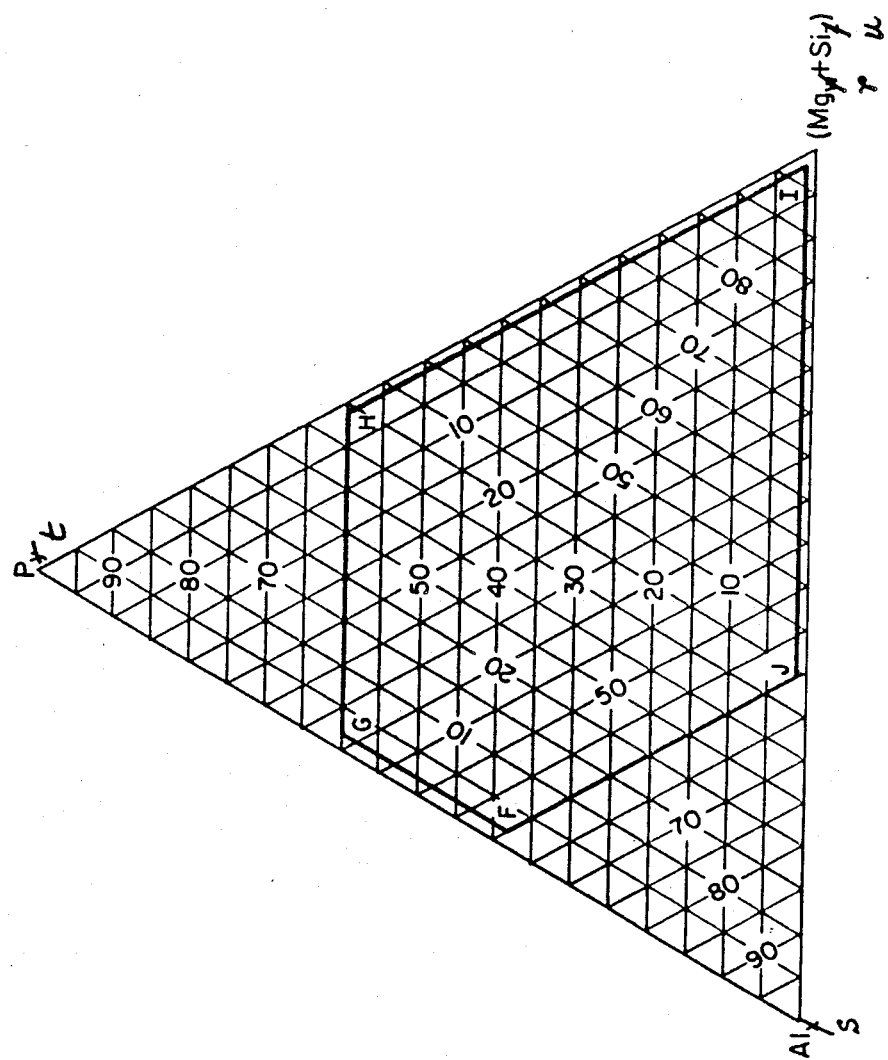
FIG. 3 is a ternary diagram wherein parameters relating to the reaction mixture employed in the preparation of the compositions of this invention are set forth as mole fractions.

In a preferred embodiment the reaction mixture is selected such that the mole fractions "r", "s", "t" and "u" are generally defined as being within the pentagonal compositional area defined by points F, G, H, I and J of the ternary diagram of FIG. 3. Points F, G, H, I and J of FIG. 3 have the following values for "r", "s", "t" and "u".

| Point | Mole Fraction | | |
|---|---|---|---|
| | s | t | (u + r) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

For reasons unknown at present, not every reaction mixture gave crystalline MgAPSO products when reaction products were examined for MgAPSO products by X-ray analysis. Those reaction mixtures from which crystalline MgAPSO products were obtained are reported in the examples hereinafter as numbered examples and those reaction mixtures from which MgAPSO products were not identified by use of X-ray analysis are reported as lettered examples.

In the foregoing expression of the reaction composition, the reactants are normalized with respect to the total of "r", "s", "t" and "u" such the (w+x+y+z)=1.00 mole, whereas in the examples the reaction mixtures are expressed in terms of molar oxide ratios and may be normalized to the moles of $P_2O_5$. This latter form is readily converted to the former form by routine calculations. Thus for example, in a reaction mixture expressed in terms of molar oxide ratios as:
2TPAOH:0.4MgO:0.8Al$_2$O$_3$:1.0P$_2$O$_5$:0.4SiO$_2$:50H$_2$O
the molar ratios of Mg, Al, P and Si are:
0.4Mg:1.6Al:2.0P:0.4Si, and (Mg+Al+P+Si)=4.4.

The mole fractions w, x, y and z are computed by dividing each coefficient and the molar proportions of water and templating by 4.4. This results in:
0.455TPAOH:(Mg$_{0.091}$Al$_{0.364}$P$_{0.455}$Si$_{0.91}$)O$_2$:11.36H$_2$O In forming reaction mixtures from which the instant molecular sieves are formed the organic templating agent, if any, can be any of those heretofore proposed for use in the synthesis of conventional aluminosilicates. In general these compounds contain elements of Group VA of the Periodic Table of Elements, particularly nitrogen, phosphorus, arsenic and antimony, preferably nitrogen or phosphorus and most preferably nitrogen where such compounds also contain at least one alkyl or aryl group having from 1 to 8 carbon atoms. Particularly preferred compounds for use as templating agents are the amines, quaternary phosphonium compounds and quaternary ammonium compounds, the latter two being represented generally by the formula R$_4$X$^+$ wherein "X" is nitrogen or phosphorus and each R is an alkyl or aryl group containing from 1 to 8 carbon atoms. Polymeric quaternary ammonium salts such as [(C$_{14}$H$_{32}$N$_2$)(OH)$_2$]$_x$ wherein "x" has a value of at least 2 are also suitably employed. The mono-, di- and triamines are advantageously utilized, either alone or in combination with a quaternary ammonium compound or other templating compound. Mixtures of two or more templating agents can either produce mixtures of the desired MgAPSOs or the more strongly directing templating species may control the course of the reaction with the other templating agents serving primarily to establish the pH conditions of the reaction gel. Representative templating agents include: tetramethylammonium; tetraethylammonium; tetrapropylammonium, tetrabutylammonium ions; tetrapentylammonium ions; di-n-propylamine; tripropylamine; triethylamine; triethanolamine; piperidine; cyclohexylamine; 2-methylpyridine; N,N-dimethylbenzylamine; N,N-dimethylethanolamine; chlorine; N,N'-dimethylpiperazine; 1,4-diazabicyclo (2,2,2,)octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo(2,2,2)octane ion; di-n-butylamine, neopentylamine; di-n-pentylamine; isopropylamine; t-butylamine; ethylenediamine; pyrrolidine; and 2-imidazolidone. Not every templating agent will direct the formation of every species of MgAPSO, i.e., a single templating agent can, with proper manipulation of the reaction conditions, direct the formation of several MgAPSO compositions, and a given MgAPSO composition can be produced using several different templating agents.

The reaction source of silicon may be silica, either as a silica sol or as fumed silica, a reactive solid amorphous precipitated silica, silica gel, alkoxides of silicon, silicic acid or alkali metal silicate and mixtures thereof.

The most suitable reactive source of phosphorus yet found for the instant process is phosphoric acid, but organic phosphates such as triethyl phosphate have been found satisfactory, and so also have crystalline or amorphous aluminophosphates such as the AlPO$_4$ composition of U.S. Pat. No. 4,310,440. Organo-phosphorus compounds, such as tetrabutylphosphonium bromide do not, apparently, serve as reactive sources of phosphorus, but these compounds may function as templating agents. It is believed that such organo-phosphorous compounds may be transformed in situ to a reactive source of phosphorus under suitable process conditions. Conventional phosphorus salts such as sodium metaphosphate, may be used, at least in part, as the phosphorus source, but are not preferred.

The preferred aluminum source is either an aluminum alkoxide, such as aluminum isoproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The reactive source of magnesium can be introduced into the reaction system in any form which permits the formation in situ of a reactive form of magnesium, i.e., reactive to form the framework tetrahedral unit $MgO_2^{-2}$. Compounds of magnesium which may be employed include oxides, hydroxides, alkoxides, nitrates, sulfates, halides, carboxylates (e.g. acetates and the like), organo-metallics and mixtures thereof.

While not essential to the synthesis of MgAPSO compositions, stirring or other moderate agitation of the reaction mixture and/or seeding the reaction mixture with seed crystals of either the MgAPSO species to be produced or a topologically similar aluminophosphate, aluminosilicate or other molecular sieve composition facilitates the crystallization procedure.

After crystallization the MgAPSO product may be isolated and advantageously washed with water and dried in air. The as-synthesized MgAPSO will typically contain within its internal pore system at least one form of any templating agent, also referred to herein as the "organic moiety", employed in its formation. Most commonly the organic moiety is present, at least in part, as a charge-balancing cation as is generally the case with as-synthesized aluminosilicate zeolites prepared from organic-containing reaction systems. It is possible, however, that some or all of the organic moiety may be an occluded molecular species in a particular MgAPSO species. As a general rule the templating agent, and hence any occluded organic species, is too large to move freely through the pore system of the MgAPSO product and must be removed by calcining the MgAPSO at temperatures of from 200° C. to 700° C. to thermally degrade the organic species. In a few instances the pores of the MgAPSO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein does not include the condition of the MgAPSO species wherein any organic moiety, i.e., species derived from the templating agent, occupying the intracrystalline pore system as a result of the hydrothermal crystallization process has been reduced by post-synthesis treatment such that the value of "m" in the composition formula:

$mR:(Mg_wAl_xP_ySi_z)O_2$ has a value of less than 0.02. The other symbols of the formula are as defined hereinabove. In those preparations in which an alkoxide is employed as the source of magnesium, aluminum, phosphorus or silicon, the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as-synthesized MgAPSO material.

Since the MgAPSO compositions are formed from $MgO_2$, $AlO_2$, $PO_2$ and $SiO_2$ tetrahedral units which, respectively, have a net charge of −2, −1, +1 and 0. The matter of cation exchangeability is considerably more complicated than in the case of zeolitic molecular sieves in which, ideally, there is a stoichiometric relationship between $AlO_2^-$ tetrahedra and charge-balancing cations. In the instant compositions, an $AlO_2^-$ tetrahedron can be balanced electrically either by association with a $PO_2^+$ tetrahedron or a simple cation such as an alkali metal cation, a proton ($H^+$), a cation of magnesium present in the reaction mixture, or an organic cation derived from the templating agent. Similarly, an $MgO_2^{-2}$ tetrahedron can be balanced electrically by association with $PO_2^+$ tetrahedra, a simple cation such as alkali metal cation, a proton ($H^+$), a cation of the magnesium, organic cations derived from the templating agent, or other divalent or polyvalent metal cations introduced from an extraneous source. It has also been postulated that non-adjacent $AlO_2^-$ and $PO_2^+$ tetrahedral pairs can be balanced by $Na^+$ and $OH^-$ respectively [Flanigen and Grose, Molecular Sieve Zeolites-I, ACS, Washington, DC (1971)]

The MgAPSO compositions of the present invention exhibit cation-exchange capacity when analyzed using ion-exchange techniques heretofore employed with zeolitic aluminosilicates and have pore diameters which are inherent in the lattice structure of each species and which are at least about 3 Å in diameter. Ion exchange of MgAPSO compositions will ordinarily be possible only after the organic moiety present as a result of synthesis has been removed from the pore system. Dehydration to remove water present in the as-synthesized MgAPSO compositions can usually be accomplished, to some degree at least, in the usual manner without removal of the organic moiety, but the absence of the organic species greatly facilitates adsorption and desorption procedures. The MgAPSO materials have various degrees of hydrothermal and thermal stability, some being quite remarkable in this regard, and will function as molecular sieve adsorbents, hydrocarbon conversion catalysts or catalyst bases.

In each example the stainless steel reaction vessel utilized was lined with the inert plastic material, polytetrafluoroethylene, to avoid contamination of the reaction mixture. In general, the final reaction mixture from which each MgAPSO composition is crystallized is prepared by forming mixtures of less than all of the reagents and thereafter incorporating into these mixtures additional reagents either singly or in the form of other intermediate mixtures of two or more reagents. In some instances the reagents admixed retain their identity in the intermediate mixture and in other cases some or all of the reagents are involved in chemical reactions to produce new reagents. The term "mixture" is applied in both cases. Further, unless otherwise specified, each intermediate mixture as well as the final reaction mixture was stirred until substantially homogeneous.

Where reaction products are subjected to X-ray analysis, the X-ray patterns are obtained using standard X-ray powder diffraction techniques. The radiation source is a high-intensity, copper target, X-ray tube operated at 50 Kv and 40 ma. The diffraction pattern from the copper K-alpha radiation and graphite monochromator is suitably recorded by an X-ray spectrometer scintillation counter, pulse height analyzer and strip chart recorder. Flat compressed powder samples are scanned at 2° (2 theta) per minute, using a two second time constant. Interplanar spacings (d) in Angstrom units are obtained from the position of the diffraction peaks expressed as $2\theta$ where $\theta$ is the Bragg angle as observed on the strip chart. Intensities are determined from the heights of diffraction peaks after subtracting background, "$I_o$" being the intensity of the strongest line or peak, and "I" being the intensity of each of the other peaks.

Alternatively, the X-ray patterns are obtained from the copper K-alpha radiation by use of computer based techniques using Siemens D-500 X-ray powder diffractometers, Siemens Type K-805 X-ray sources, available from Siemens Corporation, Cherry Hill, N.J., with appropriate computer interface.

As will be understood by those skilled in the art the determination of the parameter 2 theta is subject to both human and mechanical error, which in combination, can impose an uncertainty of about ±0.4° on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m, w, vw, v and sh which represent very strong, strong, medium, weak, very weak and shoulder, respectively.

In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The molecular sieves of the instant invention may be characterized by their x-ray powder diffraction patterns and such may have one of the x-ray patterns set forth in the following Tables A through N, wherein said x-ray patterns are for both the as-synthesized and calcined forms unless otherwise noted:

TABLE A

| $2\theta$ | (MgAPSO-5) d(Å) | Relative Intensity |
|---|---|---|
| 7.2–7.4 | 12.28–11.95 | m–vs |
| 14.6–14.95 | 6.07–5.93 | w–m |
| 19.4–19.8 | 4.58–4.48 | m |
| 20.85–21.1 | 4.26–4.21 | vw–vs |
| 22.15–22.4 | 4.01–3.97 | m–vs |
| 25.6–25.95 | 3.480–3.434 | m |

TABLE B

| $2\theta$ | (MgAPSO-11) d(Å) | Relative Intensity |
|---|---|---|
| 9.0–9.6 | 9.83–9.21 | vw–m |
| 20.8–21.2 | 4.27–4.19 | vs |
| 22.0–22.4 | 4.04–3.97 | vw–m |
| 22.4–22.8 | 3.97–3.90 | vw–vs |
| 22.8–23.1 | 3.90–3.85 | m |

TABLE C

| $2\theta$ | (MgAPSO-16) d(Å) | Relative Intensity |
|---|---|---|
| 11.4–11.5 | 7.76–7.69 | m |
| 18.7–18.8 | 4.75–4.72 | w–m |
| 21.85–22.2 | 4.07–4.00 | vs |
| 22.8–23.3 | 3.900–3.818 | w–m |
| 26.75–27.3 | 3.332–3.267 | w–m |
| 29.7–29.9 | 3.008–2.988 | w–m |

TABLE D

| $2\theta$ | (MgAPSO-20) d(Å) | Relative Intensity |
|---|---|---|
| 13.8–14.2 | 6.42–6.23 | m–vs |
| 19.6–20.15 | 6.53–4.41 | m |
| 24.1–24.7 | 3.695–3.603 | m–vs |
| 27.9–28.6 | 3.198–3.121 | w |
| 31.3–32.05 | 2.861–2.791 | w |
| 34.35–35.0 | 2.610–2.601 | w |

TABLE E

| $2\theta$ | (MgAPSO-31) d(Å) | Relative Intensity |
|---|---|---|
| 8.4–9.501 | 10.53–9.3084 | w–s |
| 20.2–20.4 | 4.40–4.35 | m |
| 22.0–22.1 | 4.040–4.022 | m |
| 22.5–22.7 | 3.952–3.92 | vs |
| 31.6–31.8 | 2.831–2.814 | w–m |

TABLE F

| $2\theta$ | (MgAPSO-34) d(Å) | Relative Intensity |
|---|---|---|
| 9.3–9.7 | 9.51–9.12 | vs |
| 15.8–16.3 | 5.61–5.44 | w–m |
| 20.25–21.0 | 4.39–4.23 | m–vs |
| 25.7–26.3 | 3.466–3.389 | vw–m |
| 30.0–30.8 | 2.979–2.903 | vw–m |
| 30.9–31.4 | 2.894–2.849 | w–m |

TABLE G

| $2\theta$ | (MgAPSO-35) d(Å) | Relative Intensity |
|---|---|---|
| 10.6–11.1 | 8.35–7.97 | m–vs |
| 13.1–13.7 | 6.76–6.46 | w–vs |
| 17.0–17.6 | 5.22–5.04 | m–s |
| 20.6–21.2 | 4.31–4.19 | vw–m |
| 21.6–22.2 | 4.11–4.00 | m–vs |
| 28.1–28.8 | 3.175–3.100 | m |

TABLE H

| $2\theta$ | (MgAPSO-36) d(Å) | Relative Intensity |
|---|---|---|
| 7.8–8.0 | 11.33–11.85 | vs |
| 16.3–16.5 | 5.44–5.37 | m |
| 18.9–19.3 | 4.70–4.60 | m |
| 20.7–20.8 | 4.29–4.27 | m |
| 22.35 | 3.981 | m |

TABLE J

| $2\theta$ | (MgAPSO-39) d(Å) | Relative Intensity |
|---|---|---|
| 9.2–9.6 | 9.61–9.21 | m |
| 13.1–13.5 | 6.76–6.56 | m |
| 17.8–18.3 | 4.98–4.85 | m |
| 20.8–21.3 | 4.27–4.17 | m–vs |
| 22.2–22.8 | 4.00–3.90 | vs |

TABLE J-continued

| 2θ | (MgAPSO-39) d(Å) | Relative Intensity |
|---|---|---|
| 30.0–30.3 | 2.979–2.950 | w–m |

TABLE K

| 2θ | (MgAPSO-43) d(Å) | Relative Intensity |
|---|---|---|
| 12.3–12.95 | 7.20–6.83 | m–vs |
| 17.3–17.45 | 5.13–5.09 | w |
| 21.45–21.6 | 4.15–4.12 | m–vs |
| 27.6–27.75 | 3.232–3.215 | m |
| 33.05–33.2 | 2.710–2.699 | vw–w |

TABLE L

| 2θ | (MgAPSO-44) d(Å) | Relative Intensity |
|---|---|---|
| 9.2–9.45 | 9.61–9.37 | vs |
| 15.9–16.1 | 5.57–5.50 | m |
| 17.2–18.0 | 5.16–4.93 | vw–m |
| 20.5–20.75 | 4.33–4.28 | m–vs |
| 24.3–25.0 | 3.663–3.562 | w–m |
| 30.5–31.0 | 2.931–2.885 | w–m |

TABLE M

| 2θ | (MgAPSO-46) d(Å) | Relative Intensity |
|---|---|---|
| 7.2–8.1 | 12.28–10.92 | vs |
| 21.2–21.8 | 4.19–4.08 | w–m |
| 22.5–23.0 | 3.952–3.867 | vw–w |
| 26.6–27.2 | 3.351–3.278 | vw–w |
| 28.5–29.0 | 3.132–3.079 | vw–w |

TABLE N

| 2θ | (MgAPSO-47) d(Å) | Relative Intensity |
|---|---|---|
| 9.5–9.65 | 9.33–9.17 | vs |
| 12.85–13.05 | 6.89–6.79 | vw–m |
| 16.0–16.2 | 5.54–5.46 | w–m |
| 20.6–20.85 | 4.32–4.26 | m–s |
| 24.75–25.3 | 3.598–3.526 | vw–m |
| 30.55–30.95 | 2.925–2.889 | w–m |

PREPARATIVE REAGENTS

In the following examples the MgAPSO compositions were prepared using numerous reagents. The reagents employed and abbreviations employed herein, if any, for such reagents are as follows:

(a) Alipro: aluminum isoproxide;
(b) CATAPAL: Trademark of Condea for hydrated pseudo-boehmite;
(c) LUDOX LS: Trademark of DuPont for an aqueous solution of 30 weight percent $SiO_2$ and 0.1 weight percent $Na_2O$;
(d) $Mg(Ac)_2$: magnesium acetate tetrahydrate, $Mg(C_2H_3O_2)_2 \cdot 4H_2O$;
(e) $H_3PO_4$: 85 weight percent phosphoric acid in water;
(f) TBAOH: tetrabutylammonium hydroxide (40 wt.% in water);
(g) $Pr_2NH$: di-n-propylamine;
(h) $Pr_3N$: tri-n-propylamine;
(i) Quin: Quinuclidine;
(j) MQuin: Methyl Quinuclidine hydroxide (17.9% in water);
(k) C-hex; cyclohexylamine;
(l) TEAOH; tetraethylammonium hydroxide (40 wt. % in water).
(m) DEEA: diethylethanolamine;
(n) i-$Pr_2NH$: di-isopropylamine;
(o) TEABr: tetraethylammonium bromide; and
(p) TPAOH: tetrapropylammonium hydroxide (40 wt. % in water).

PREPARATIVE PROCEDURE

The MgAPSO compositions were prepared by preparing reaction mixtures having a molar composition expressed as:

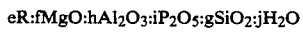

$$eR : fMgO : hAl_2O_3 : iP_2O_5 : gSiO_2 : jH_2O$$

wherein e, f, g, h, i and j represent the moles of template R, magnesium (expressed as the oxide), $SiO_2$, $Al_2O_3$, $P_2O_5$ ($H_3PO_4$ expressed as $P_2O_5$) and $H_2O$, respectively. The values for e, f, g, h, i and j were as set forth in the hereinafter discussed preparative examples.

The reaction mixtures were prepared by three procedures, designated hereinafter as Methods A, B and C, unless otherwise noted in the preparative examples.

Method A was employed for examples 1–25, 27–30, 39–46, 55–57, 61, 63–71, 77–85 and 87–106. Method B was employed for examples 31–38 and 47–54. Method C was employed for examples 26, 62 and 72–76. The aluminum source was aluminum iso-propoxide except that CATAPAL was the aluminum source in examples 39–55 and 58–61.

Method A

The reaction mixture was prepared by mixing the ground aluminum source (Al-ipro or CATAPAL) with the $H_3PO_4$ and water on a gradual basis with occasional cooling with an ice bath. The resulting mixture was blended until a homogeneous mixture was observed. When the aluminum source was CATAPAL the water and $H_3PO_4$ were first mixed and the CATAPAL added thereto. The magnesium acetate was dissolved in a portion of the water and was then added followed by addition of the LUDOX-LS. The combined mixture was blended until a homogenous mixture was observed. The organic templating agent was added to this mixture and blended until a homogenous mixture was observed. The resulting mixture (final reaction mixture) was placed in a lined (polytetrafluoroethylene) stainless steel pressure vessel and digested at a temperature (150° C. or 200° C.) for an effective time. Alternatively, if the digestion temperature was 100° C. the final reaction mixture was placed in a lined (polytetrafluoroethylene) screw top bottle for a time. All digestions were carried out at the autogenous pressure. The products were removed from the reaction vessel cooled and evaluated as set forth hereinafter.

Method B

When method B was employed the organic templating agent was di-n-propylamine. The aluminum source, silicon source and one-half of the water were first mixed and blended until a homogeneous mixture was observed. A second solution was prepared by mixing the remaining water, the $H_3PO_4$ and the magnesium acetate. The magnesium acetate and $H_3PO_4$ solution was then added to the above mixture and blended until a homogeneous mixture was observed. The organic templating agent(s) was then added and the resulting reaction mixture digested and product recovered as was done in Method A.

Method C

Method C was carried out by mixing aluminum iso-propoxide, LUDOX LS and water in a blender or by mixing water and aluminum iso-propoxide in a blender followed by addition of the LUDOX LS. $H_3PO_4$ and magnesium acetate were then added to this mixture. The organic templating agent was then added to the resulting mixture and digested and product recovered as was done in Method A.

The following examples are provided to further illustrate the invention and are not intended to be limiting thereof.

EXAMPLES 1 TO 90 AND A TO R

MgAPSO molecular sieves were prepared according to the above described Methods A, B and C by preparing reaction mixtures expressed as $$eR:fMgO:hAl_2O_3:iP_2O_5:gSiO_2:jH_2O$$

wherein, e, f, h, i, g and j represent the moles of template R, magnesium (expressed as the oxide), $Al_2O_3$, $SiO_2$, $P_2O_5$ ($H_3PO_3$ expressed as $P_2O_5$), and $H_2O$ respectively. The values for e, f, g, h and i for examples 1 to 90 are set forth in Table I–VI. The value of "j" was 50 in examples 1 to 84 and 87–90 and was 75 in example 85 and was 71 in example 86. Tables I–VI also shows the temperature (°C.) and time (hours) employed for digestion and indicates the final MgAPSO(s) formed.

Examples A to R represent reaction mixtures wherein crystalline MgAPSO products were not observed when the reaction products were subjected to X-ray analysis. The results of Examples A to R are set forth in Table VII.

TABLE I

| Example | Template | e | f | h | i | g | Temp (°C.) | Time(hrs) | MgAPSO Product(s)[2] |
|---|---|---|---|---|---|---|---|---|---|
| 1 | Pr$_3$N | 1.0 | 0.2 | 0.9 | 0.9 | 0.2 | 150 | 48 | MgAPSO-5; MgAPSO-36 |
| 2 | Pr$_3$N | 1.0 | 0.2 | 0.9 | 0.9 | 0.2 | 150 | 166 | MgAPSO-5; MgAPSO-36 |
| 3 | Pr$_3$N | 1.0 | 0.2 | 0.9 | 0.9 | 0.2 | 200 | 48 | MgAPSO-5; MgAPSO-36 |
| 4 | Pr$_3$N | 1.0 | 0.2 | 0.9 | 0.9 | 0.6 | 200 | 166 | MgAPSO-5; MgAPSO-36 |
| 5[1,3] | Pr$_3$N | 1.0 | 0.2 | 0.9 | 0.9 | 0.6 | 150 | 88 | MgAPSO-36; MgAPSO-5 |
| 6[1,3] | Pr$_3$N | 1.0 | 0.2 | 0.9 | 0.9 | 0.6 | 200 | 88 | MgAPSO-36; MgAPSO-5 |
| 7[3] | Pr$_3$N | 1.5 | 0.2 | 0.9 | 0.9 | 0.6 | 150 | 48 | MgAPSO-5; MgAPSO-36; |
| 8[3] | Pr$_3$N | 1.5 | 0.2 | 0.9 | 0.9 | 0.6 | 150 | 160 | MgAPSO-5; MgAPSO-36 |
| 9[3] | Pr$_3$N | 1.5 | 0.9 | 0.9 | 0.9 | 0.6 | 200 | 48 | MgAPSO-5; MgAPSO-36 |
| 10[3] | Pr$_3$N | 1.5 | 0.2 | 0.9 | 0.9 | 0.6 | 200 | 160 | MgAPSO-5; MgAPSO-36 |
| 11[3] | TPAOH | 1.0 | 0.2 | 0.9 | 0.9 | 0.6 | 150 | 48 | MgAPSO-5; |
| 12[3] | TPAOH | 1.0 | 0.2 | 0.9 | 0.9 | 0.6 | 150 | 112 | MgAPSO-5; |
| 13[3] | TPAOH | 1.0 | 0.2 | 0.9 | 0.9 | 0.6 | 200 | 48 | MgAPSO-5; MgAPSO-36 |
| 14[3] | TPAOH | 1.0 | 0.2 | 0.9 | 0.9 | 0.6 | 200 | 112 | MgAPSO-5; MgAPSO-36 |

[1]Seed crystal of MAPO-36 employed, as disclosed in copending U.S. Ser. No. 514,334.
[2]Major species as identified by x-ray diffraction pattern of product, except that when two or more species were identified the species are listed in the order of their predominance in the MgAPSO products.
[3]LUDOX-LS was added before the magnesium acetate in this example.

TABLE II

| Example | Template | e | f | h | i | g | Temp (°C.) | Time(hrs) | MgAPSO Product(s)[1] |
|---|---|---|---|---|---|---|---|---|---|
| 15[2] | DEEA | 1.0 | 0.2 | 0.9 | 0.9 | 0.6 | 150 | 88 | MgAPSO-5; MgAPSO-47 |
| 16[2] | DEEA | 1.0 | 0.2 | 0.9 | 0.9 | 0.6 | 200 | 88 | MgAPSO-5; MgAPSO-47 |
| 17 | Pr$_2$NH | 1.0 | 0.2 | 0.9 | 0.9 | 0.2 | 150 | 48 | MgAPSO-11; MgAPSO-5; |
| 18 | Pr$_2$NH | 1.0 | 0.2 | 0.9 | 0.9 | 0.2 | 150 | 166 | MgAPSO-11; MgAPSO-5; MgAPSO-39; MgAPSO-46 |
| 19 | Pr$_2$NH | 1.0 | 0.2 | 0.9 | 0.9 | 0.2 | 200 | 48 | MgAPSO-5; MgAPSO-11; MgAPSO-39 |
| 20 | Pr$_2$NH | 1.0 | 0.2 | 0.9 | 0.9 | 0.2 | 200 | 166 | MgAPSO-11; MgAPSO-39; MgAPSO-5 |
| 21 | Pr$_2$NH | 1.0 | 0.1 | 0.95 | 0.8 | 0.4 | 125 | 300 | MgAPSO-11 |
| 22 | Pr$_2$NH | 1.0 | 0.1 | 0.95 | 0.8 | 0.4 | 150 | 47 | MgAPSO-39; MgAPSO-11; MgAPSO-46; MgAPSO-31 |
| 23 | Pr$_2$NH | 1.0 | 0.1 | 0.95 | 0.8 | 0.4 | 150 | 165 | MgAPSO-39; MgAPSO-46; MgAPSO-11; MgAPSO-31 |
| 24 | Pr$_2$NH | 1.0 | 0.1 | 0.95 | 0.8 | 0.4 | 200 | 47 | MgAPSO-11; MgAPSO-5; MgAPSO-39; MgAPSO-31 |
| 25 | Pr$_2$NH | 1.0 | 0.1 | 0.95 | 0.8 | 0.4 | 200 | 165 | MgAPSO-11; MgAPSO-5; MgAPSO-46 |
| 26 | Pr$_2$NH | 1.0 | 0.4 | 1.0 | 1.0 | 0.4 | 150 | 182 | MgAPSO-46 |
| 27[2] | Pr$_2$NH | 2.0 | 0.9 | 0.9 | 0.2 | 0.2 | 150 | 96 | MgAPSO-46 |
| 28[2] | Pr$_2$NH | 2.0 | 0.9 | 0.9 | 0.2 | 0.2 | 150 | 238 | MgAPSO-46; MgAPSO-11 |
| 29[2] | Pr$_2$NH | 2.0 | 0.9 | 0.9 | 0.2 | 0.2 | 200 | 96 | MgAPSO-11; MgAPSO-46; MgAPSO-39 |

[1]Major species as identified by x-ray diffraction pattern of product, except that when two or more species were identified the species are listed in the order of their predominance in the MgAPSO products.
[2]LUDOX-LS was added before the magnesium acetate in this example.

TABLE III

| Example | Template | e | f | h | i | g | Temp (°C.) | Time(hrs) | MgAPSO Product(s)[1] |
|---|---|---|---|---|---|---|---|---|---|
| 30[2] | Pr₂NH | 2.0 | 0.9 | 0.9 | 0.2 | 0.2 | 200 | 238 | MgAPSO-11; MgAPSO-46; MgAPSO-39; MgAPSO-33 |
| 31 | Pr₂NH | 1.5 | 0.2 | 0.9 | 0.9 | 0.2 | 150 | 144 | MgAPSO-39; MgAPSO-11; MgAPSO-46 |
| 32 | Pr₂NH | 1.5 | 0.2 | 0.9 | 0.9 | 0.2 | 200 | 144 | MgAPSO-39; MgAPSO-11; MgAPSO-46 |
| 33 | Pr₂NH | 1.5 | 0.2 | 0.9 | 0.9 | 0.2 | 150 | 144 | MgAPSO-39; MgAPSO-11; MgAPSO-46 |
| 34 | Pr₂NH | 1.5 | 0.2 | 0.9 | 0.9 | 0.2 | 200 | 144 | MgAPSO-39; MgAPSO-11; MgAPSO-46 |
| 35 | Pr₂NH | 1.0 | 0.2 | 2.7 | 0.9 | 0.2 | 150 | 142 | MgAPSO-39; MgAPSO-11 |
| 36 | Pr₂NH | 1.0 | 0.2 | 2.7 | 0.9 | 0.2 | 200 | 142 | MgAPSO-11; MgAPSO-39; MgAPSO-46 |
| 37 | Pr₂NH | 2.0 | 0.2 | 2.7 | 0.9 | 0.2 | 150 | 142 | MgAPSO-46 |
| 38 | Pr₂NH | 2.0 | 0.2 | 2.7 | 0.9 | 0.2 | 200 | 142 | MgAPSO-46 |
| 39[2] | Pr₂NH | 1.0 | 0.2 | 0.9 | 0.9 | 0.2 | 150 | 96 | MgAPSO-11; MgAPSO-39; MgAPSO-46 |
| 40[2] | Pr₂NH | 1.0 | 0.2 | 0.9 | 0.9 | 0.2 | 150 | 190 | MgAPSO-11; MgAPSO-39; MgAPSO-46 |
| 41[2] | Pr₂NH | 1.0 | 0.2 | 0.9 | 0.9 | 0.2 | 200 | 96 | MgAPSO-11; MgAPSO-39; MgAPSO-46 |
| 42[2] | Pr₂NH | 1.0 | 0.2 | 0.9 | 0.9 | 0.2 | 200 | 190 | MgAPSO-11; MgAPSO-39; MgAPSO-46 |
| 43[2] | Pr₂NH | 2.0 | 0.2 | 0.9 | 0.9 | 0.2 | 150 | 96 | MgAPSO-46; MgAPSO-20 |
| 44[2] | Pr₂NH | 2.0 | 0.2 | 0.9 | 0.9 | 0.2 | 150 | 190 | MgAPSO-46 |
| 45[2] | Pr₂NH | 2.0 | 0.2 | 0.9 | 0.9 | 0.2 | 200 | 96 | MgAPSO-39; MgAPSO-46 |
| 46[2] | Pr₂NH | 2.0 | 0.2 | 0.9 | 0.9 | 0.2 | 200 | 190 | MgAPSO-39; MgAPSO-46 |

[1]Major species as identified by x-ray diffraction pattern of product, except that when two or more species were identified the species are listed in the order of their predominance in the MgAPSO products.
[2]LUDOX-LS was added before the magnesium acetate in this example.

TABLE IV

| Example | Template | e | f | h | i | g | Temp (°C.) | Time(hrs) | MgAPSO Product(s)[4] |
|---|---|---|---|---|---|---|---|---|---|
| 47 | Pr₂NH | 1.0 | 0.2 | 0.9 | 0.9 | 0.2 | 150 | 94 | MgAPSO-11; MgAPSO-39; MgAPSO-5 |
| 48 | Pr₂NH | 1.0 | 0.2 | 0.9 | 0.9 | 0.2 | 150 | 238 | MgAPSO-11; MgAPSO-39; MgAPSO-5 |
| 49 | Pr₂NH | 1.0 | 0.2 | 0.9 | 0.9 | 0.2 | 200 | 94 | MgAPSO-11; MgAPSO-39; MgAPSO-5 |
| 50 | Pr₂NH | 1.0 | 0.2 | 0.9 | 0.9 | 0.2 | 200 | 238 | MgAPSO-11; MgAPSO-5; MgAPSO-39; MgAPSO-46 |
| 51 | Pr₂NH | 2.0 | 0.2 | 0.9 | 0.9 | 0.2 | 150 | 94 | MgAPSO-46; MgAPSO-39; MgAPSO-5 |
| 52 | Pr₂NH | 2.0 | 0.2 | 0.9 | 0.9 | 0.2 | 150 | 238 | MgAPSO-46; MgAPSO-11; MgAPSO-39 |
| 53 | Pr₂NH | 2.0 | 0.2 | 0.9 | 0.9 | 0.2 | 200 | 94 | MgAPSO-46 |
| 54 | Pr₂NH | 2.0 | 0.2 | 0.9 | 0.9 | 0.2 | 200 | 238 | MgAPSO-46; MgAPSO-39 |
| 55[1,2] | Pr₂NH | 2.0 | 0.2 | 0.9 | 0.9 | 0.2 | 150, 200 | 113 | MgAPSO-39; MgAPSO-31; MgAPSO-11 |
| 56 | i-Pr₂NH | 1.0 | 0.2 | 0.9 | 0.9 | 0.2 | 150 | 88 | MgAPSO-5; MgAPSO-11; MgAPSO-34 |
| 57 | i-Pr₂NH | 1.0 | 0.2 | 0.9 | 0.9 | 0.2 | 200 | 88 | MgAPSO-5; MgAPSO-11; MgAPSO-34 |
| 58[3,5] | i-Pr₂NH | 1.0 | 0.2 | 0.9 | 0.9 | 0.2 | 150 | 96 | MgAPSO-5; MgAPSO-11; MgAPSO-39 |
| 59[3,5] | i-Pr₂NH | 1.0 | 0.2 | 0.9 | 0.9 | 0.2 | 200 | 96 | MgAPSO-5; MgAPSO-11; MgAPSO-39 |
| 60[5] | i-Pr₂NH | 1.0 | 0.17 | 0.92 | 0.95 | 0.1 | 150 | 93 | MgAPSO-5; MgAPSO-11 |
| 61[5] | i-Pr₂NH | 1.0 | 0.17 | 0.92 | 0.95 | 0.1 | 200 | 93 | MgAPSO-5; MgAPSO-39; MgAPSO-11 |
| 62 | i-Pr₂NH | 1.0 | 0.4 | 1.0 | 1.0 | 0.4 | 150 | 231 | MgAPSO-5; MgAPSO-11 |

[1]AlPO₄-31 seed crystal
[2]Two mixtures were digested with one at 150° C. and one at 200° C.
[3]SAPO-11 seed crystal as disclosed in U.S. Ser. No. 400,438
[4]Major species as identified by x-ray diffraction pattern of product, except that when two or more species were identified the species are listed in the order of their predominance in the MgAPSO products.
[5]LUDOX-LS was added before magnesium acetate in this example.

TABLE V

| Example | Template | e | f | h | i | g | Temp (°C.) | Time (hrs) | MgAPSO Product(s)[1] |
|---|---|---|---|---|---|---|---|---|---|
| 63 | TEAOH | 1.0 | 0.2 | 0.9 | 0.9 | 0.2 | 150 | 48 | MgAPSO-34 |
| 64 | TEAOH | 1.0 | 0.2 | 0.9 | 0.9 | 0.2 | 150 | 166 | MgAPSO-34 |
| 65 | TEAOH | 1.0 | 0.2 | 0.9 | 0.9 | 0.2 | 200 | 48 | MgAPSO-34; MgAPSO-5 |
| 66 | TEAOH | 1.0 | 0.2 | 0.9 | 0.9 | 0.2 | 200 | 166 | MgAPSO-34 |
| 67 | TEAOH | 1.0 | 0.2 | 0.9 | 0.9 | 0.6 | 150 | 40 | MgAPSO-34; MgAPSO-5 |
| 68 | TEAOH | 1.0 | 0.2 | 0.9 | 0.9 | 0.6 | 150 | 121 | MgAPSO-34 |
| 69 | TEAOH | 1.0 | 0.2 | 0.9 | 0.9 | 0.6 | 200 | 40 | MgAPSO-5; MgAPSO-34 |
| 70 | TEAOH | 1.0 | 0.2 | 0.9 | 0.9 | 0.6 | 200 | 121 | MgAPSO-5; MgAPSO-34 |
| 71 | TEAOH | 1.0 | 0.2 | 0.9 | 0.9 | 0.6 | 150 | 114 | MgAPSO-34; MgAPSO-5 |
| 72 | TEAOH | 1.0 | 0.4 | 1.0 | 1.0 | 0.4 | 100 | 111 | MgAPSO-34 |
| 73 | TEAOH | 1.0 | 0.4 | 1.0 | 1.0 | 0.4 | 100 | 182 | MgAPSO-34 |
| 74 | TEAOH | 1.0 | 0.4 | 1.0 | 1.0 | 0.4 | 150 | 111 | MgAPSO-34 |
| 75 | TEAOH | 1.0 | 0.4 | 1.0 | 1.0 | 0.4 | 150 | 182 | MgAPSO-34 |
| 76 | TEAOH | 1.0 | 0.4 | 1.0 | 1.0 | 0.4 | 150 | 231 | MgAPSO-34; MgAPSO-5 |

[1]Major species as identified by x-ray diffraction pattern of product, except that when two or more species were indentified the species are listed in the order of their predominance in the MgAPSO products.

TABLE VI

| Example | Template | e | f | h | i | g | Temp (°C.) | Time (hrs) | MgAPSO Product(s)[1] |
|---|---|---|---|---|---|---|---|---|---|
| 77 | Quin | 1.0 | 0.2 | 0.9 | 0.9 | 0.2 | 150 | 48 | MgAPSO-35; MgAPSO-16 |
| 78 | Quin | 1.0 | 0.2 | 0.9 | 0.9 | 0.2 | 150 | 166 | MgAPSO-35; MgAPSO-16 |

TABLE VI-continued

| Example | Template | e | f | h | i | g | Temp (°C.) | Time (hrs) | MgAPSO Product(s)[1] |
|---|---|---|---|---|---|---|---|---|---|
| 79 | Quin | 1.0 | 0.2 | 0.9 | 0.9 | 0.2 | 200 | 48 | MgAPSO-35; MgAPSO-16 |
| 80 | Quin | 1.0 | 0.2 | 0.9 | 0.9 | 0.2 | 200 | 166 | MgAPSO-35; MgAPSO-16 |
| 81 | MQuin | 1.0 | 0.2 | 0.9 | 0.9 | 0.2 | 150 | 40 | MgAPSO-35 |
| 82 | MQuin | 1.0 | 0.2 | 0.9 | 0.9 | 0.2 | 150 | 121 | MgAPSO-35 |
| 83 | MQuin | 1.0 | 0.2 | 0.9 | 0.9 | 0.2 | 200 | 40 | MgAPSO-35 |
| 84 | MQuin | 1.0 | 0.2 | 0.9 | 0.9 | 0.2 | 200 | 121 | MgAPSO-35 |
| 85 | MQuin | 1.0 | 0.2 | 0.9 | 0.9 | 0.6 | 150 | 114 | MgAPSO-35; MgAPSO-16 |
| 86[2] | TBAOH | 2.0 | 0.4 | 0.8 | 1.0 | 0.4 | 200 | 48 | MgAPSO-5 |
| 87[3] | C-hex | 1.0 | 0.2 | 0.9 | 0.9 | 0.6 | 150 | 40 | MgAPSO-44; MgAPSO-5 |
| 88[3] | C-hex | 1.0 | 0.2 | 0.9 | 0.9 | 0.6 | 200 | 107 | MgAPSO-44; MgAPSO-5 |
| 89[3] | C-hex | 1.0 | 0.2 | 0.9 | 0.9 | 0.6 | 150 | 40 | MgAPSO-5; MgAPSO-44 |
| 90[3] | C-hex | 1.0 | 0.2 | 0.9 | 0.9 | 0.6 | 200 | 107 | MgAPSO-5; MgAPSO-44 |

[1] Major species as identified by x-ray diffraction pattern of product, except that when two or more species were identified the species are listed in the order of their predominance in the MgAPSO products.
[2] The mixing order in this example was in the order of the aluminum source, magnesium source, silicon source and the phosphorus source.
[3] LUDOX-LS was added before the magnesium acetate in this example.

TABLE VII

| Example[1] | Template | e | f | h | i | g | j | Temp (°C.) | Time (hrs) | Method |
|---|---|---|---|---|---|---|---|---|---|---|
| A | TPABr | 1.0 | 0.4 | 1.0 | 1.0 | 0.4 | 50 | 150 | 231 | C |
| B | Pr$_2$NH | 1.0 | 0.1 | 0.95 | 0.8 | 0.4 | 50 | 125 | 47 | A |
| C | Pr$_2$NH | 1.0 | 0.1 | 0.95 | 0.8 | 0.4 | 50 | 125 | 165 | A |
| D | Pr$_2$NH | 1.0 | 0.4 | 1.0 | 1.0 | 0.4 | 50 | 100 | 111 | C |
| E | Pr$_2$NH | 1.0 | 0.4 | 1.0 | 1.0 | 0.4 | 50 | 100 | 182 | C |
| F | Pr$_2$NH | 1.0 | 0.4 | 1.0 | 1.0 | 0.4 | 50 | 150 | 111 | C |
| G | Pr$_2$NH | 1.0 | 0.2 | 0.9 | 0.9 | 0.2 | 50 | 150 | 96 | B |
| H | Pr$_2$NH | 1.0 | 0.2 | 0.9 | 0.9 | 0.2 | 50 | 150 | 235 | B |
| I | Pr$_2$NH | 1.0 | 0.2 | 0.9 | 0.9 | 0.2 | 50 | 200 | 96 | B |
| J | Pr$_2$NH | 1.0 | 0.2 | 0.9 | 0.9 | 0.2 | 50 | 200 | 235 | B |
| K | Pr$_2$NH | 2.0 | 0.2 | 0.9 | 0.9 | 0.2 | 50 | 150 | 96 | B |
| L | Pr$_2$NH | 2.0 | 0.2 | 0.9 | 0.9 | 0.2 | 50 | 150 | 235 | B |
| M | Pr$_2$NH | 2.0 | 0.2 | 0.9 | 0.9 | 0.2 | 50 | 200 | 96 | B |
| N | Pr$_2$NH | 2.0 | 0.2 | 0.9 | 0.9 | 0.2 | 50 | 200 | 235 | B |
| O | TBAOH | 2.0 | 0.4 | 0.8 | 1.0 | 0.4 | 71 | 150 | 48 | (2) |
| P | TBAOH | 2.0 | 0.4 | 0.8 | 1.0 | 0.4 | 71 | 150 | 160 | (2) |
| Q | TBAOH | 2.0 | 0.4 | 0.8 | 1.0 | 0.4 | 71 | 200 | 160 | (2) |

[1] Reaction mixtures from which crystalline MgAPSO products were not identified by X-ray analysis of the products.
[2] The mixing order in this example was in the order of the aluminum source, magnesium source, silicon source and the phosphorous source.

EXAMPLES 91 TO 106

MgAPSO molecular sieves were prepared according to the procedures employed in examples 1 to 90. The aluminum source was CATAPAL in examples 96, and 97.

The results of preparative examples 91 to 106 are set forth in Table VIII.

EXAMPLE 107

Samples of the MgAPSO products were subjected to chemical analysis. The chemical analysis for each of the analyzed products is given hereinafter:

(a) The chemical analysis for the MgAPSO-5 of example 4 was:

TABLE VIII

| Example[2] | Template | e | f | h | i | g | Temp (°C.) | Time (hrs) | MgAPSO Product(s)[1] |
|---|---|---|---|---|---|---|---|---|---|
| 91 | MQuin | 1.0 | 0.1 | 0.9 | 0.9 | 0.6 | 150 | 450 | MgAPSO-35 |
| 92 | TEAOH | 1.0 | 0.1 | 0.9 | 0.9 | 0.6 | 150 | 44 | MgAPSO-5; MgAPSO-34 |
| 93 | TEAOH | 1.0 | 0.1 | 0.9 | 0.9 | 0.6 | 150 | 44 | MgAPSO-5; MgAPSO-34 |
| 94 | TEAOH | 1.0 | 0.05 | 1.0 | 1.0 | 0.4 | 100 | 280 | MgAPSO-34 |
| 95 | TEAOH | 1.0 | 0.1 | 1.0 | 1.0 | 0.4 | 100 | 280 | MgAPSO-34 |
| 96 | Pr$_2$NH | 2.0 | 0.1 | 0.9 | 0.9 | 0.6 | 150 | 122 | MgAPSO-43; MgAPSO-46 |
| 97 | Pr$_2$NH | 2.0 | 0.1 | 0.9 | 0.9 | 0.6 | 150 | 122 | MgAPSO-43; MgAPSO-46 |
| 98 | Quin | 1.0 | 0.2 | 0.9 | 0.9 | 0.6 | 220 | 114 | MgAPSO-16; MgAPSO-35 |
| 99 | C-hex | 1.0 | 0.2 | 0.9 | 0.9 | 0.6 | 220 | 114 | MgAPSO-44; MgAPSO-5 |
| 100 | TMAOH | 1.0 | 0.2 | 0.9 | 0.7 | 0.6 | 100 | 18 | MgAPSO-20 |
| 101 | TMAOH | 1.0 | 0.2 | 0.9 | 0.7 | 0.6 | 150 | 111 | MgAPSO-20 |
| 102 | TMAOH | 1.0 | 0.2 | 0.9 | 0.7 | 0.6 | 200 | 22 | MgAPSO-20 |
| 103 | TMAOH | 1.0 | 0.2 | 0.9 | 0.7 | 0.6 | 200 | 111 | MgAPSO-20 |
| 104 | DEEA | 2.0 | 0.2 | 0.9 | 0.7 | 0.6 | 100 | 111 | MgAPSO-47 |
| 105 | DEEA | 2.0 | 0.2 | 0.9 | 0.7 | 0.6 | 100 | 22 | MgAPSO-47; MgAPSO-5 |
| 106 | DEEA | 2.0 | 0.2 | 0.9 | 0.7 | 0.6 | 100 | 111 | MgAPSO-47 |

[1] Major species as identified by x-ray diffraction pattern of product, except that when two or more species were identified the species are listed in the order of their predominance in the MgAPSO products.
[2] LUDOX-LS was added before the magnesium acetate in examples 91 to 106.

| Component | Weight Percent |
|---|---|
| Al$_2$O$_3$ | 31.3 |
| P$_2$O$_5$ | 45.4 |
| MgO | 2.8 |
| SiO$_2$ | 3.9 |
| Carbon | 5.0 |
| LOI* | 13.7 |

*LOI = Loss on Ignition

The above chemical analysis gives an overall product composition in molar oxide ratios (anydrous basis) of: 0.23 MgO:1.00 Al$_2$O$_3$:1.04 P$_2$O$_5$:0.21 SiO$_2$; and a formula (anhydrous basis) of:

$$0.03R(Mg_{0.05}Al_{0.44}P_{0.46}Si_{0.05})O_2$$

(b) The chemical analysis for MgAPSO-36 of example 5 was:

| Component | Weight Percent |
|---|---|
| Al$_2$O$_3$ | 31.2 |
| P$_2$O$_5$ | 44.6 |
| MgO | 2.6 |
| SiO$_2$ | 8.6 |
| Carbon | 6.2 |
| LOI* | 13.9 |

*LOI = Loss on Ignition

The above chemical analysis gives an overall product composition in molar oxide ratios (anhydrous basis) of: 0.21 MgO; 1.00 Al$_2$O$_3$:1.03 P$_2$O$_5$:0.45 SiO$_2$; and a formula (anhydrous basis) of:

$$0.04R(Mg_{0.05}Al_{0.43}P_{0.44}Si_{0.10})O_2$$

(c) The chemical analysis for the MgAPSO-46 of example 44 was:

| Component | Weight Percent |
|---|---|
| Al$_2$O$_3$ | 30.1 |
| P$_2$O$_5$ | 38.4 |
| MgO | 4.1 |
| SiO$_2$ | 4.4 |
| Carbon | 10.6 |
| LOI* | 22.5 |

*LOI = Loss on Ignition

The above chemical analysis gives an overall product composition in molar oxide ratios (anhydrous basis) of: 0.34 MgO; 1.00 Al$_2$O$_3$:0.92 P$_2$O$_5$:0.25 SiO$_2$: and a formula (anhydrous basis) of:

$$0.11R(Mg_{0.08}Al_{0.45}P_{0.41}Si_{0.06})O_2$$

(d) The chemical analysis of the MgAPSO-34 of example 63 was:

| Component | Weight Percent |
|---|---|
| Al$_2$O$_3$ | 31.7 |
| P$_2$O$_5$ | 37.0 |
| MgO | 3.0 |
| SiO$_2$ | 2.9 |
| Carbon | 8.3 |
| LOI* | 21.6 |

*LOI = Loss on Ignition

The above chemical analysis gives an overall product composition in molar oxide ratios (anhydrous basis) of: 0.24 MgO; 1.00 Al$_2$O$_3$:0.84 P$_2$O$_5$:0.16 SiO$_2$; and a formula (anhydrous basis) of:

$$0.07R(Mg_{0.06}Al_{0.49}P_{0.41}Si_{0.04})O_2$$

(e) The chemical analysis for the MgAPSO-34 of example 68 was:

| Component | Weight Percent |
|---|---|
| Al$_2$O$_3$ | 29.8 |
| P$_2$O$_5$ | 40.4 |
| MgO | 2.3 |
| SiO$_2$ | 6.9 |
| Carbon | 10.4 |
| LOI* | 21.1 |

*LOI = Loss on Ignition

The above chemical analysis gives an overall product composition in molar oxide ratios (anhydrous basis) of: 0.20 MgO; 1.00 Al$_2$O$_3$:0.97 P$_2$O$_5$:0.39 SiO$_2$: and a formula (anhydrous basis) of:

$$0.08R(Mg_{0.04}Al_{0.44}P_{0.43}Si_{0.09})O_2$$

(f) The chemical analysis of the MgAPSO-34 of example 74 was:

| Component | Weight Percent |
|---|---|
| Al$_2$O$_3$ | 28.6 |
| P$_2$O$_5$ | 33.9 |
| MgO | 4.9 |
| SiO$_2$ | 3.7 |
| Carbon | 9.0 |
| LOI* | 27.1 |

*LOI = Loss on Ignition

The above chemical analysis gives an overall product composition in molar oxide ratios (anhydrous basis) of: 0.43 MgO; 1.00 Al$_2$O$_3$:0.85 P$_2$O$_5$:0.22 SiO$_2$; and a formula (anhydrous basis) of:

$$0.08R(Mg_{0.10}Al_{0.46}P_{0.38}Si_{0.05})O_2$$

(g) The chemical analysis for the MgAPSO-35 of example 85 was:

| Component | Weight Percent |
|---|---|
| Al$_2$O$_3$ | 28.3 |
| P$_2$O$_5$ | 42.7 |
| MgO | 2.8 |
| SiO$_2$ | 4.0 |
| Carbon | 9.8 |
| LOI* | 19.6 |

*LOI = Loss on Ignition

The above chemical analysis gives an overall product composition in molar oxide ratios of: 0.37R:0.25 MgO; 1.0 Al$_2$O$_3$; 1.08 P$_2$O$_5$; 0.24 SiO$_2$; and a formula (anhydrous basis) of:

$$0.08(Mg_{0.05}Al_{0.43}P_{0.47}Si_{0.05})O_2$$

(h) The chemical analysis for the MgAPSO-20 of example 101 was:

| Component | Weight Percent |
|---|---|
| Al$_2$O$_3$ | 27.8 |

-continued

| Component | Weight Percent |
|---|---|
| P$_2$O$_5$ | 31.4 |
| MgO | 3.1 |
| SiO$_2$ | 15.2 |
| Carbon | 9.7 |
| LOI* | 21.2 |

*LOI = Loss on Ignition

The above chemical analysis gives an overall product composition in molar oxide ratios (anhydrous basis) of: 0.74R:0.28 MgO; 1.00 Al$_2$O$_3$:0.81 P$_2$O$_5$:0.93 SiO$_2$; and a formula (anhydrous basis) of:

$$0.15R(Mg_{0.06}Al_{0.41}P_{0.34}Si_{0.19})O_2$$

(i) The chemical analysis for the MgAPSO-43 of example 97 was:

| Component | Weight Percent |
|---|---|
| Al$_2$O$_3$ | 32.3 |
| P$_2$O$_5$ | 33.1 |
| MgO | 3.6 |
| SiO$_2$ | 8.2 |
| Carbon | 9.1 |
| LOI* | 21.1 |

*LOI = Loss on Ignition

The above chemical analysis gives an overall product composition in molar oxide ratios (anhydrous basis) of: 0.40R:0.28 MgO; 1.00 Al$_2$O$_3$:0.74 P$_2$O$_5$:0.43 SiO$_2$; and a formula (anhydrous basis) of:

$$0.10R(Mg_{0.07}Al_{0.48}P_{0.35}Si_{0.10})O_2$$

(j) The chemical analysis for the MgAPSO-47 of example 104 was:

| Component | Weight Percent |
|---|---|
| Al$_2$O$_3$ | 33.1 |
| P$_2$O$_5$ | 29.3 |
| MgO | 2.8 |
| SiO$_2$ | 7.7 |
| Carbon | 5.7 |
| LOI* | 25.4 |

*LOI = Loss on Ignition

The above chemical analysis gives an overall product composition in molar oxide ratios (anhydrous basis): of: 0.24R:0.21 MgO; 1.00 Al$_2$O$_3$:0.64 P$_2$O$_5$:0.39 SiO$_2$; and a formula (anhydrous basis) of:

$$0.06R(Mg_{0.06}Al_{0.51}P_{0.33}Si_{0.10})O_2$$

EXAMPLE 108

EDAX (energy dispersive analysis by x-ray) microprobe analysis in conjunction with SEM (scanning electron microscope) was carried out on clear crystals from the products of examples. Analysis of crystals having a morphology characteristic of the MgAPSO products as prepared in the following referenced examples gave the following analysis based on relative peak heights:

| | Average of Spot Probes |
|---|---|
| (a) MgAPSO-5 (Example 4): | |
| Mg | 3 |
| Al | 46 |
| P | 48 |
| Si | 3 |
| (b) MgAPSO-36 (Example 5): | |
| Mg | 3 |
| Al | 40 |
| P | 48 |
| Si | 9 |
| (c) MgAPSO-46 (Example 44): | |
| Mg | 5 |
| Al | 39 |
| P | 49 |
| Si | 6 |
| (d) MgAPSO-34 (Example 63): | |
| Mg | 6 |
| Al | 44 |
| P | 45 |
| Si | 6 |
| (e) MgAPSO-34 (Example 75): | |
| Mg | 6 |
| Al | 42 |
| P | 44 |
| Si | 8 |
| (f) MgAPSO-35 (Example 80): | |
| Mg | 4 |
| Al | 41 |
| P | 51 |
| Si | 4 |
| (g) MgAPSO-47 (Example 104): | |
| Mg | 2 |
| Al | 42 |
| P | 43 |
| Si | 13 |

EXAMPLE 109

Samples of the MgAPSO products were evaluated for adsorption capacities in the as-synthesized form or were calcined in air or nitrogen, to remove at least part of the organic templating agent, as hereinafter set forth. The adsorption capacities of each as-synthesized or calcined sample were measured using a standard McBain-Bakr gravimetric adsorption apparatus. The samples were activated in a vacuum at 350° C. prior to measurement. The McBain-Bakr data for the selected MgAPSO products were:

(a) Example 4 (MgAPSO-5)

| Adsorbate | Kinetic Diameter, Å | Pressure (Torr) | Temp (°C.) | Wt. % Adsorbed* |
|---|---|---|---|---|
| O$_2$ | 3.46 | 99 | −183 | 13.2 |
| O$_2$ | 3.46 | 749 | −183 | 15.5 |
| Cyclohexane | 6.0 | 57 | 23.4 | 7.9 |
| neopentane | 6.2 | 100 | 23.4 | 5.0 |
| H$_2$O | 2.65 | 4.6 | 23.2 | 16.0 |
| H$_2$O | 2.65 | 16.8 | 23.5 | 21.3 |

*calcined in air at 600° C. for 2.25 hrs.

The above data demonstrate that the pore size of the calcined product is greater than about 6.2 Å.

(b) Example 101 (MgAPSO-20)

| Adsorbate | Kinetic Diameter, Å | Pressure (Torr) | Temp (°C.) | Wt. % Adsorbed* |
|---|---|---|---|---|
| O$_2$ | 3.46 | 99 | −183 | 0.8 |
| O$_2$ | 3.46 | 750 | −183 | 2.7 |
| H$_2$O | 2.65 | 4.6 | 23.2 | 16.5 |

-continued

| Adsorbate | Kinetic Diameter, Å | Pressure (Torr) | Temp (°C.) | Wt. % Adsorbed* |
|---|---|---|---|---|
| $H_2O$ | 2.65 | 16.8 | 23.5 | 19.9 |

*calcined in air at 600° C. for 1.5 hrs.

The above data demonstrate that the pore size of the calcined product is about 3.0 Å.

(c) Example 63 (MgAPSO-34)

| Adsorbate | Kinetic Diameter, Å | Pressure (Torr) | Temp (°C.) | Wt. % Adsorbed* |
|---|---|---|---|---|
| $O_2$ | 3.46 | 100 | −183 | 21.7 |
| $O_2$ | 3.46 | 734 | −183 | 33.6 |
| isobutane | 5.0 | 300 | 23 | 1.3 |
| n-hexane | 4.3 | 51 | 24 | 10.4 |
| $H_2O$ | 2.65 | 4.6 | 23 | 27.1 |
| $H_2O$ | 2.65 | 18.5 | 24 | 32.9 |

*calcined in air at 600° C. for 1.5 hours.

The above data demonstrate that the pore size of the calcined product is about 4.3 Å.

(d) Example 84 (MgAPSO-35)

| Adsorbate | Kinetic Diameter, Å | Pressure (Torr) | Temp (°C.) | Wt. % Adsorbed* |
|---|---|---|---|---|
| $O_2$ | 3.46 | 100 | −183 | 6.7 |
| $O_2$ | 3.46 | 734 | −183 | 9.2 |
| isobutane | 5.0 | 100 | 24 | 0.3 |
| n-hexane | 4.3 | 51 | 24 | 1.1 |
| $H_2O$ | 2.65 | 4.6 | 23 | 11.5 |
| $H_2O$ | 2.65 | 19.5 | 23 | 17.7 |

*calcined in nitrogen at 500° C. for 2 hrs.

(e) Example 91 (MgAPSO-35)

| Adsorbate | Kinetic Diameter, Å | Pressure (Torr) | Temp (°C.) | Wt. % Adsorbed* |
|---|---|---|---|---|
| $O_2$ | 3.46 | 100 | −183 | 11.2 |
| $O_2$ | 3.46 | 744 | −183 | 14.0 |
| isobutane | 5.0 | 100 | 22.8 | 0.2 |
| n-hexane | 4.3 | 49 | 22.3 | 5.7 |
| $H_2O$ | 2.65 | 4.6 | 23.1 | 16.1 |
| $H_2O$ | 2.65 | 17.8 | 22.9 | 20.5 |

*calcined at 500° in air for 6.7 hours.

The above data demonstrate that the pore size of the calcined product is about 4.3 Å. In addition, the data demonstrate that in part (d) the template was not sufficiently removed by the calcination.

(f) Example 5 (MgAPSO-36)

| Adsorbate | Kinetic Diameter, Å | Pressure (Torr) | Temp (°C.) | Wt. % Adsorbed* |
|---|---|---|---|---|
| $O_2$ | 3.46 | 100 | −183 | 12.9 |
| $O_2$ | 3.46 | 734 | −183 | 15.4 |
| isobutane | 5.0 | 100 | 24 | 5.2 |
| cyclohexane | 6.0 | 59 | 23.7 | 9.0 |
| neopentane | 6.2 | 100 | 24.5 | 5.5 |
| $H_2O$ | 2.65 | 4.6 | 23 | 16.8 |
| $H_2O$ | 2.65 | 20 | 23.6 | 23.5 |

*calcined in air at 500° C. for 2.0 hrs. and in air at 600° C. for two additional hours.

The above data demonstrate that the pore size of the calcined product is greater than 6.2 Å.

(g) Example 44 (MgAPSO-64)

| Adsorbate | Kinetic Diameter, Å | Pressure (Torr) | Temp (°C.) | Wt. % Adsorbed* |
|---|---|---|---|---|
| $O_2$ | 3.46 | 100 | −183 | 20.7 |
| $O_2$ | 3.46 | 734 | −183 | 24.7 |
| neopentane | 6.2 | 100 | 24.5 | 8.4 |
| isobutane | 5.0 | 100 | 24 | 7.8 |
| cyclo-hexane | 6.0 | 59 | 23.7 | 11.9 |
| $H_2O$ | 2.65 | 4.6 | 23 | 22.0 |
| $H_2O$ | 2.65 | 20.0 | 23.6 | 27.4 |

*calcined in nitrogen at 500° C. for 1.75 hours.

The above data demonstrate that the pore size of the calcined product is greater than about 6.2 Å.

(h) Example 104 (MgAPSO-47)

| Adsorbate | Kinetic Diameter, Å | Pressure (Torr) | Temp (°C.) | Wt. % Adsorbed* |
|---|---|---|---|---|
| $O_2$ | 3.46 | 99 | −183 | 14.1 |
| $O_2$ | 3.46 | 725 | −183 | 29.2 |
| isobutane | 5.0 | 100 | 22.8 | 0.2 |
| n-hexane | 4.3 | 49 | 23.3 | 4.2 |
| $H_2O$ | 2.65 | 4.6 | 23.1 | 18.5 |
| $H_2O$ | 2.65 | 17.8 | 22.9 | 28.7 |

*calcined in air at 500° C. for 1.75 hours.

The above data demonstrate that the pore size of the calcined product is about 4.3 Å.

EXAMPLE 110

(a) MgAPSO-5, as prepared to in example 4, was subjected to x-ray analysis. MgAPSO-5 was determined to have a characteristic x-ray powder diffraction pattern which contains the d-spacings set forth below:

| $2\theta$ | d, (Å) | 100 × I/Io |
|---|---|---|
| 7.35 | 11.71 | 83 |
| 7.9* | 11.19 | (sh) |
| 12.8 | 6.92 | 11 |
| 14.8 | 5.99 | 18 |
| 15.8* | 5.61 | 1 |
| 16.4* | 5.40 | 2 |
| 19.0* | 4.67 | (sh) |
| 19.65 | 4.52 | 48–52 |
| 21.0 | 4.23 | 54 |
| 22.2 | 4.004 | 100 |
| 23.6* | 3.770 | 1 |
| 24.7 | 3.604 | 4 |
| 25.75 | 3.460 | 31 |
| 27.2* | 3.278 | 3 |
| 28.9 | 3.089 | 20 |
| 29.8 | 2.998 | 18 |
| 31.8* | 2.814 | 1 |
| 33.5 | 2.675 | 5 |
| 34.4 | 2.607 | 17 |
| 36.8 | 2.442 | 4 |
| 37.6 | 2.392 | 11 |
| 40.7 | 2.217 | 1 |
| 41.3 | 2.186 | 3 |
| 42.05 | 2.149 | 4 |
| 42.85 | 2.110 | 3 |
| 43.4 | 2.085 | 2 |
| 44.8 | 2.023 | 2 |
| 45.4 | 1.998 | 2 |
| 47.4 | 1.918 | 6 |
| 51.1 | 1.787 | 2 |
| 51.7 | 1.768 | 2 |
| 52.4 | 1.746 | 1 |
| 55.2 | 1.664 | 4 |

*impurity peak (b) A portion of the as-synthesized MgAPSO-5 of part (a) was calcined in air at 600° C. for about 2.25 hours. The calcined product was characterized by the x-ray power diffusion pattern below:

| 2θ | d, (Å) | 100 × I/Io |
|---|---|---|
| 7.4 | 11.95 | 94 |
| 7.9** | 11.19 | sh |
| 8.2** | 10.78 | sh |
| 12.9 | 6.86 | 20 |
| 14.9 | 5.95 | 8 |
| 16.4** | 5.40 | 2 |
| 19.3** | 4.60 | sh |
| 19.8 | 4.48 | 33 |
| 21.1 | 4.21 | 52 |
| 22.4 | 3.969 | 100 |
| 24.8 | 3.590 | 4 |
| 26.0 | 3.427 | 27 |
| 27.1** | 3.290 | 2 |
| 27.9** | 3.198 | 2 |
| 28.3* | 3.154 | 2 |
| 29.1 | 3.069 | 20 |
| 30.15 | 2.964 | 15 |
| 33.7 | 2.660 | 5 |
| 34.6 | 2.592 | 18 |
| 37.0 | 2.430 | 4 |
| 37.8 | 2.380 | 10 |
| 41.6 | 2.171 | 1 |
| 42.4 | 2.132 | 1 |
| 42.9 | 2.108 | 1 |
| 43.6 | 2.076 | 1 |
| 45.0 | 2.015 | 1 |
| 46.2 | 1.965 | 1 |
| 47.8 | 1.903 | 4 |
| 50.9 | 1.794 | 1 |
| 51.6 | 1.771 | 1 |
| 55.8 | 1.648 | 2 |

*peak may contain impurity
**impurity peak (c) The MgAPSO-5 compositions are generally characterized by the data in Table IX below:

TABLE IX

| 2θ | d, (Å) | Relative Intensity |
|---|---|---|
| 7.2–7.4 | 12.28–11.95 | m–vs |
| 14.6–14.95 | 6.07–5.93 | w–m |
| 19.4–19.8 | 4.58–4.48 | m |
| 20.85–21.1 | 4.26–4.21 | vw–vs |
| 22.15–22.4 | 4.01–3.97 | m–vs |
| 25.6–25.95 | 3.480–3.434 | m |

(d) The MgAPSO-5 compositions for which x-ray powder diffraction data have been obtained to date have patterns which are characterized by the x-ray powder diffraction pattern shown in Table X, below:

TABLE X

| 2θ | d, (Å) | 100 × I/Io |
|---|---|---|
| 7.2–7.4 | 12.28–11.95 | 69–100 |
| 12.65–12.9 | 7.00–6.86 | 8–12 |
| 14.6–14.95 | 6.07–5.93 | 15–35 |
| 19.4–19.8 | 4.58–4.48 | 38–73 |
| 20.85–21.1 | 4.26–4.21 | (sh)–100 |
| 22.15–22.4 | 4.013–3.969 | 48–100 |
| 24.4–24.85 | 3.648–3.583 | 0–14 |
| 25.6–25.95 | 3.480–3.434 | 23–44 |
| 28.7–29.1 | 3.110–3.069 | 12–20 |
| 29.65–30.15 | 3.013–2.964 | 15–21 |
| 33.4–33.75 | 2.683–2.656 | 2–11 |
| 34.2–34.65 | 2.622–2.589 | 11–19 |
| 36.6–37.0 | 2.455–2.430 | 0–4 |
| 37.4–37.8 | 2.405–2.380 | 5–11 |
| 40.6–40.7 | 2.222–2.217 | 0–1 |
| 41.1–41.6 | 2.196–2.171 | 0–3 |
| 41.85–42.4 | 2.159–2.132 | 3–4 |
| 42.6–43.05 | 2.122–2.101 | 0–3 |

TABLE X-continued

| 2θ | d, (Å) | 100 × I/Io |
|---|---|---|
| 43.2–43.5 | 2.094–2.080 | 0–2 |
| 44.6–45.0 | 2.032–2.015 | 0–2 |
| 45.3–45.6 | 2.002–1.989 | 0–2 |
| 46.1–46.35 | 1.969–1.959 | 0–1 |
| 47.2–47.75 | 1.926–1.905 | 4–6 |
| 50.4 | 1.811 | 0–1 |
| 50.9–51.1 | 1.794–1.787 | 0–3 |
| 51.6–51.9 | 1.771–1.762 | 0–4 |
| 52.2–52.4 | 1.752–1.746 | 0–1 |
| 55.2–55.8 | 1.664–1.648 | 0–4 |

EXAMPLE 11

(a) MgAPSO-11, as prepared to in example 17, was subjected to x-ray analysis. MgAPSO-11 was determined to have a characteristic x-ray powder diffraction pattern which contains the d-spacings set forth below:

| 2θ | d, (Å) | 100 × I/Io |
|---|---|---|
| 7.3** | 12.11 | 47 |
| 8.0 | 8.04 | 19 |
| 9.3 | 9.51 | 30 |
| 12.8** | 6.92 | (sh) |
| 13.1 | 6.76 | 13 |
| 14.75** | 6.01 | 6 |
| 15.6 | 5.68 | 20 |
| 16.1 | 5.51 | 3 |
| 18.8 | 4.72 | 3 |
| 19.6** | 4.53 | 15 |
| 20.25 | 4.39 | 32 |
| 21.0* | 4.23 | 100 |
| 22.0 | 4.040 | (sh) |
| 22.3** | 3.987 | 57 |
| 22.6 | 3.934 | (sh) |
| 23.0 | 3.867 | 46 |
| 24.4** | 3.648 | sh |
| 24.6 | 3.619 | 9 |
| 25.7** | 3.467 | 11 |
| 26.3 | 3.389 | 20 |
| 28.5** | 3.132 | 11 |
| 28.85 | 3.095 | 11 |
| 29.35* | 3.043 | 4 |
| 29.8 | 2.998 | 9 |
| 31.4 | 2.849 | 6 |
| 32.7 | 2.739 | 13 |
| 34.1 | 2.629 | 10 |
| 34.3** | 2.614 | sh |
| 36.2** | 2.481 | 4 |
| 37.6* | 2.392 | 12 |
| 39.3 | 2.293 | 3 |
| 40.6 | 2.222 | 1 |
| 41.9* | 2.156 | 2 |
| 42.9 | 2.108 | 4 |
| 44.6 | 2.032 | 3 |
| 54.4 | 1.687 | 1 |

*Peak may contain impurity
**Impurity peak (b) A portion of the as-synthesized MgAPSO-11 of part (a) was calcined in air at 600° C. for about 2 hours. The calcined product was characterized by the x-ray powder diffraction pattern below:

| 2θ | d, (Å) | 100 × I/Io |
|---|---|---|
| 7.4* | 11.95 | 30 |
| 8.1 | 10.92 | 35 |
| 9.6 | 9.21 | 35 |
| 13.0 | 6.81 | 19 |
| 15.8 | 5.61 | 30 |
| 18.2* | 4.87 | 4 |
| 19.7* | 4.51 | 9 |
| 20.15 | 4.41 | 22 |
| 21.2 | 4.19 | 100 |

-continued

| 2θ | d, (Å) | 100 × I/Io |
|---|---|---|
| 22.3 | 3.987 | 74 |
| 22.9 | 3.883 | sh |
| 23.35 | 3.810 | 43 |
| 26.0* | 3.427 | sh |
| 26.3 | 3.389 | 17 |
| 26.7 | 3.339 | sh |
| 28.8 | 3.100 | sh |
| 29.0* | 3.079 | 17 |
| 29.5 | 3.028 | 9 |
| 30.0* | 2.979 | 4 |
| 31.0* | 2.885 | 3 |
| 31.7 | 2.823 | 15 |
| 32.6 | 2.747 | 15 |
| 33.8 | 2.652 | 3 |
| 34.1* | 2.629 | 15 |
| 36.2 | 2.481 | 12 |
| 37.9 | 2.374 | 15 |
| 43.2 | 2.094 | 4 |

*Impurity Peak (c) The MgAPSO-11 compositions are generally characterized by the data of Table XI below:

TABLE XI

| 2θ | d, (Å) | Relative Intensity |
|---|---|---|
| 9.0–9.6 | 9.83–9.21 | vw–m |
| 20.8–21.2 | 4.27–4.19 | vs |
| 22.0–22.4 | 4.04–3.97 | vw–m |
| 22.4–22.8 | 3.97–3.90 | vw–vs |
| 22.8–23.1 | 3.90–3.85 | m |

(d) The MgAPSO-11 compositions for which x-ray powder diffraction data have been obtained to date have patterns which are characterized by the x-ray powder diffraction pattern shown in Table XII, below:

TABLE XII

| 2θ | d, (Å) | 100 × I/Io |
|---|---|---|
| 7.8–8.15 | 11.33–10.85 | sh–35 |
| 9.0–9.6 | 9.83–9.21 | 6–60 |
| 12.9–13.2 | 6.86–6.71 | sh–22 |
| 15.4–15.9 | 5.75–5.57 | sh–30 |
| 15.95–16.35 | 5.56–5.42 | sh–3 |
| 18.7–19.1 | 4.75–4.65 | 0–4 |
| 20.0–20.5 | 4.44–4.33 | sh–38 |
| 20.8–21.2 | 4.27–4.19 | 100 |
| 22.0–22.4 | 4.040–3.969 | sh–72 |
| 22.4–22.8 | 3.969–3.900 | sh–90 |
| 22.8–23.1 | 3.900–3.850 | 21–48 |
| 23.35 | 3.810 | 0–4 |
| 24.4–24.9 | 3.648–3.576 | 0–9 |
| 26.2–26.7 | 3.401–3.339 | 0–21 |
| 28.4–28.8 | 3.143–3.100 | sh–17 |
| 29.3–29.5 | 3.048–3.028 | 0–6 |
| 29.6–30.0 | 3.018–2.979 | 0–17 |
| 31.2–31.7 | 2.867–2.823 | 0–15 |
| 32.4–32.8 | 2.763–2.730 | 0–18 |
| 33.8–34.5 | 2.652–2.600 | 9–13 |
| 35.7 | 2.515 | 0–3 |
| 36.1–36.8 | 2.488–2.442 | 0–11 |
| 37.5–37.9 | 2.398–2.374 | 0–17 |
| 39.15–39.6 | 2.301–2.276 | 0–3 |
| 40.25–40.75 | 2.241–2.214 | 0–1 |
| 41.2–41.4 | 2.191–2.181 | 0–1 |
| 41.8–42.1 | 2.161–2.146 | 0–4 |
| 42.8–43.2 | 2.113–2.094 | 0–5 |
| 44.5–44.9 | 2.036–2.019 | 0–4 |
| 50.3–50.7 | 1.814–1.801 | 0–3 |
| 54.4–54.6 | 1.687–1.681 | 0–3 |

EXAMPLE 112

(a) MgAPSO-16, as prepared to in example 93, was subjected to x-ray analysis. MgAPSO-16 was determined to have a characteristic x-ray powder diffraction pattern which contains the d-spacings set forth below:

| 2θ | d, (Å) | 100 × I/Io |
|---|---|---|
| 8.6** | 10.30 | 13 |
| 10.95** | 8.10 | 36 |
| 11.45 | 7.73 | 64 |
| 13.3** | 6.66 | 24 |
| 15.85** | 5.60 | 6 |
| 17.25** | 5.14 | 50 |
| 17.75** | 4.99 | 9 |
| 18.7 | 4.74 | 45 |
| 20.4** | 4.35 | 35 |
| 20.75** | 4.28 | 10 |
| 21.1** | 4.21 | 26 |
| 21.55** | 4.12 | sh |
| 21.85* | 4.07 | 100 |
| 23.05* | 3.858 | 26 |
| 26.3** | 3.391 | 5 |
| 26.75* | 3.332 | 25 |
| 28.45** | 3.135 | 17 |
| 28.65** | 3.116 | 18 |
| 29.0* | 3.079 | 17 |
| 29.9 | 2.987 | 20 |
| 32.0** | 2.796 | 30 |
| 32.85 | 2.727 | 3 |
| 34.6** | 2.592 | 6 |
| 34.85 | 2.573 | 4 |
| 35.65** | 2.519 | 12 |
| 37.9* | 2.373 | 8 |
| 39.95* | 2.256 | 5 |
| 42.0** | 2.152 | 4 |
| 42.9** | 2.108 | 4 |
| 44.3* | 2.044 | 4 |
| 48.55* | 1.876 | 10 |
| 49.35** | 1.846 | 5 |
| 51.4** | 1.778 | 5 |
| 52.2** | 1.752 | 2 |
| 52.5 | 1.743 | 2 |
| 55.0** | 1.670 | 5 |

*Peak may contain impurity
**Impurity peak (b) A portion of the as-synthesized MgAPSO-16 of part (a) was calcined in air at 600° C. for about 2 hours. The calcined product was characterized by the x-ray powder diffraction pattern below:

| 2θ | d, (Å) | 100 I/Io |
|---|---|---|
| 8.7** | 10.16 | 25 |
| 11.0** | 8.04 | 185 |
| 11.4 | 7.76 | sh |
| 13.6** | 6.51 | 200 |
| 17.5** | 5.07 | 50 |
| 18.7 | 4.75 | 10 |
| 21.2** | 4.23 | 45 |
| 22.2* | 4.004 | 100 |
| 22.8* | 3.900 | 15 |
| 23.7** | 3.754 | 30 |
| 25.1** | 3.548 | 15 |
| 26.4** | 3.376 | 15 |
| 27.3* | 3.267 | 40 |
| 28.7** | 3.110 | 65 |
| 29.0* | 3.079 | sh |
| 29.7 | 3.008 | 45 |
| 32.0** | 2.797 | 15 |
| 32.6** | 2.747 | 50 |
| 33.2 | 2.706 | sh |
| 34.6* | 2.592 | 10 |
| 35.6** | 2.522 | 5 |

*Peak may contain impurity
**Impurity peak (c) The MgAPSO-16 compositions are characterized by the data of Table XIII below

TABLE XIII

| 2θ | d, (Å) | Relative Intensity |
|---|---|---|
| 11.4–11.5 | 7.76–7.69 | m |
| 18.7–18.8 | 4.75–4.72 | w–m |
| 21.85–22.2 | 4.07–4.00 | vs |
| 22.8–23.3 | 3.900–3.818 | w–m |
| 26.75–27.3 | 3.332–3.267 | w–m |
| 29.7–29.9 | 3.008–2.988 | w–m |

(d) The MgAPSO-16 compositions for which x-ray powder diffraction data have been obtained to date have patterns which are characterized by the x-ray powder diffraction pattern shown in Table XIV, below:

TABLE XIV

| 2θ | d, (Å) | 100 × I/Io |
|---|---|---|
| 11.5–11.5 | 7.76–7.69 | sh–64 |
| 18.7–18.8 | 4.75–4.72 | 10–45 |
| 21.85–22.2 | 4.07–4.00 | 100 |
| 22.8–23.3 | 3.900–3.818 | 15–26 |
| 26.75–27.3 | 3.332–3.267 | 16–40 |
| 28.95–29.0 | 3.084–3.079 | sh–17 |
| 29.7–29.9 | 3.008–2.988 | 9–45 |
| 32.8–33.2 | 2.730–2.968 | sh–3 |
| 34.6–34.85 | 2.592–2.573 | 4–10 |
| 37.8–38.0 | 2.380–2.368 | 4–7 |
| 39.4–39.95 | 2.287–2.256 | 2–5 |
| 44.3–44.5 | 2.044–2.036 | 2–10 |
| 48.55–48.6 | 1.876–1.873 | 7–10 |
| 52.4–52.5 | 1.746–1.743 | 1–2 |

EXAMPLE 113

(a) MgAPSO-20, as prepared in example 98, was subjected to x-ray analysis. MgAPSO-20 was determined to have a characteristic x-ray powder diffraction pattern which contains the d-spacings set forth below:

| 2θ | d, (Å) | 100 × I/Io |
|---|---|---|
| 13.9 | 6.36 | 44 |
| 19.75 | 4.50 | 42 |
| 22.05 | 4.029 | 3 |
| 24.2 | 3.676 | 100 |
| 28.0 | 3.184 | 12 |
| 31.4 | 2.849 | 10 |
| 34.5 | 2.601 | 14 |
| 37.35 | 2.408 | 1 |
| 38.45* | 2.340 | 1 |
| 40.0 | 2.253 | 4 |
| 42.55 | 2.124 | 5 |
| 47.3 | 1.921 | 4 |
| 49.0* | 1.859 | 1 |
| 49.4* | 1.846 | 2 |
| 51.7 | 1.768 | 8 |

*impurity peak (b) A portion of the as-synthesized MgAPSO-20 of part (a) was calcined in air at 600° C. for about 1.5 hours. The calcined product was characterized by the x-ray powder diffraction pattern of below:

| 2θ | d, (Å) | 100 × I/Io |
|---|---|---|
| 14.15 | 7.27 | 100 |
| 20.05 | 4.43 | 20 |
| 22.45 | 3.964 | 4 |
| 24.6 | 3.616 | 54 |
| 28.5 | 3.132 | 15 |
| 32.0 | 2.799 | 10 |
| 35.0 | 2.564 | 10 |

(c) The MgAPSO-20 compositions are characterized by the data of Table XV below:

TABLE XV

| 2θ | d, (Å) | Relative Intensity |
|---|---|---|
| 13.8–14.2 | 6.42–6.23 | m–vs |
| 19.6–20.15 | 6.53–4.41 | m |
| 24.1–24.7 | 3.695–3.603 | m–vs |
| 27.9–28.6 | 3.198–3.121 | w |
| 31.3–32.05 | 2.861–2.791 | w |
| 34.35–35.0 | 2.610–2.601 | w |

(d) The MgAPSO-20 compositions for which x-ray powder diffraction data have been obtained to date have patterns which are characterized by the x-ray powder diffraction pattern shown in Table XVI, below:

TABLE XVI

| 2θ | d, (Å) | 100 × I/Io |
|---|---|---|
| 13.8–14.2 | 6.42–6.23 | 42–100 |
| 19.6–20.15 | 4.55–4.41 | 22–43 |
| 21.95–22.45 | 4.050–3.964 | 3–7 |
| 24.1–24.7 | 3.695–3.603 | 56–100 |
| 27.9–28.6 | 3.198–3.121 | 11–15 |
| 31.3–32.05 | 2.861–2.791 | 10–12 |
| 34.35–35.0 | 2.610–2.601 | 10–16 |
| 37.2–37.35 | 2.417–2.408 | 1–2 |
| 39.9–40.0 | 2.260–2.253 | 3–4 |
| 42.4–42.55 | 2.130–2.124 | 5 |
| 47.15–47.3 | 1.927–1.921 | 4–5 |
| 51.55–51.7 | 1.772–1.768 | 8 |

EXAMPLE 114

(a) MgAPSO-34, as prepared in example 68, was subjected to x-ray analysis. MgAPSO-34 was determined to have a characteristic x-ray powder diffraction pattern which contains the d-spacings set forth below:

| 2θ | d, (Å) | 100 × I/Io |
|---|---|---|
| 9.5 | 9.32 | 100 |
| 12.8 | 6.91 | 15 |
| 14.1 | 6.30 | 15 |
| 16.0 | 5.55 | 52 |
| 17.95 | 4.94 | 21 |
| 20.5 | 4.32 | 92 |
| 22.2 | 4.002 | 4 |
| 23.0 | 3.864 | 5 |
| 25.15 | 3.540 | 23 |
| 25.8 | 3.455 | 18 |
| 27.5 | 3.243 | 3 |
| 28.3 | 3.151 | 4 |
| 29.5 | 3.029 | 4 |
| 30.5 | 2.932 | 33 |
| 31.2 | 2.866 | 22 |
| 31.6* | 2.833 | 5 |
| 32.25 | 2.775 | 3 |
| 34.35 | 2.611 | 7 |
| 38.6 | 2.332 | 2 |
| 36.2 | 2.480 | 8 |
| 39.6 | 2.277 | 4 |
| 43.1 | 2.100 | 3 |
| 47.5 | 1.915 | 4 |
| 48.9 | 1.862 | 6 |
| 50.9 | 6.795 | 4 |
| 53.0 | 1.727 | 4 |
| 54.5 | 1.684 | 2 |
| 55.75 | 1.649 | 4 |

*impurity peak (b) A portion of the as-synthesized MgAPSO-34 of part (a) was calcined in air at 550° C. for about 2 hours. The calcined product was characterized by the x-ray powder diffraction pattern below:

| 2θ | d,(Å) | 100 × I/Io |
|---|---|---|
| 9.7 | 9.12 | 100 |
| 13.1 | 6.76 | 22 |
| 14.2 | 6.24 | 1 |
| 16.3 | 5.44 | 15 |
| 18.1 | 4.90 | 10 |
| 19.3 | 4.60 | 3 |
| 20.95 | 4.24 | 31 |
| 21.6* | 4.11 | sh |
| 22.4 | 3.969 | 3 |
| 23.35 | 3.809 | 3 |
| 25.35 | 3.513 | 11 |
| 26.3 | 3.389 | 10 |
| 28.5 | 3.132 | 4 |
| 30.0 | 2.979 | sh |
| 31.0 | 2.885 | 23 |
| 33.8 | 2.652 | 2 |
| 35.0 | 2.564 | 3 |
| 36.6 | 2.455 | 1 |
| 43.7 | 2.071 | 1 |
| 49.4 | 1.845 | 2 |
| 51.3 | 1.781 | 2 |
| 52.2 | 1.752 | 1 |
| 53.1 | 1.725 | 1 |
| 54.0 | 1.698 | 2 |

*impurity peak (c) The MgAPSO-34 compositions are characterized by the date of Table XVII below:

TABLE XVII

| 2θ | d, (Å) | Relative Intensity |
|---|---|---|
| 9.3–9.7 | 9.51–9.12 | vs |
| 15.8–16.3 | 5.61–5.44 | w–m |
| 20.25–21.0 | 4.39–4.23 | m–vs |
| 25.7–26.3 | 3.466–3.389 | vw–m |
| 30.0–30.8 | 2.979–2.903 | vw–m |
| 30.9–31.4 | 2.894–2.849 | w–m |

(d) The MgAPSO-34 compositions for which x-ray powder diffraction data have been obtained to date have patterns which are characterized by the x-ray powder diffraction pattern shown in Table XVIII below.

TABLE XVIII

| 2θ | d, (Å) | 100 × I/Io |
|---|---|---|
| 9.3–9.7 | 9.51–9.12 | 99–100 |
| 12.6–13.1 | 7.03–6.76 | 11–25 |
| 13.8–14.3 | 6.42–6.19 | 0–24 |
| 15.8–16.3 | 5.61–5.44 | 13–56 |
| 17.8–18.2 | 4.98–4.87 | 5–28 |
| 19.1–19.4 | 4.65–4.58 | 0–3 |
| 20.25–21.0 | 4.39–4.23 | 22–100 |
| 22.2–22.5 | 4.004–3.952 | 0–6 |
| 22.8–23.4 | 3.900–3.802 | 0–6 |
| 24.9–25.4 | 3.576–3.507 | 6–27 |
| 25.7–26.3 | 3.466–3.389 | 6–29 |
| 27.4–28.0 | 3.255–3.187 | 0–4 |
| 28.2–28.8 | 3.164–3.100 | 0–4 |
| 29.0–29.6 | 3.079–3.018 | 0–6 |
| 30.0–30.8 | 2.979–2.903 | 0–34 |
| 30.9–31.4 | 2.894–2.849 | 16–30 |
| 32.2–32.4 | 2.780–2.763 | 0–4 |
| 33.8–34.5 | 2.401–2.600 | 0–15 |
| 34.6–35.0 | 2.592–2.564 | 0–4 |
| 36.0–36.6 | 2.495–2.456 | 0–4 |
| 38.4–39.0 | 2.344–2.309 | 0–2 |
| 43.0–43.7 | 2.103–2.071 | 0–3 |
| 44.6–45.0 | 2.032–2.015 | 0–1 |
| 47.2–47.6 | 1.926–1.910 | 0–4 |
| 48.3–49.4 | 1.884–1.845 | 0–6 |
| 50.2 | 1.817 | 0–2 |
| 50.7–51.4 | 1.801–1.778 | 0–4 |
| 51.3–51.5 | 1.781–1.774 | 0–2 |
| 52.9–53.1 | 1.731–1.725 | 0–4 |
| 54.1–54.6 | 1.695–1.681 | 0–4 |

TABLE XVIII-continued

| 2θ | d, (Å) | 100 × I/Io |
|---|---|---|
| 55.5–55.9 | 1.656–1.645 | 0–4 |

EXAMPLE 115

(a) MgAPSO-35, as prepared in example 85, was subjected to x-ray analysis. MgAPSO-35 was determined to have a characteristic x-ray powder diffraction powder which contains the d-spacings set forth below:

| 2θ | d, (Å) | 100 × I/Io |
|---|---|---|
| 8.6 | 10.28 | 11 |
| 10.9 | 8.12 | 44 |
| 11.4** | 7.76 | 2 |
| 13.4 | 6.61 | 20 |
| 15.9 | 5.57 | 9 |
| 17.3 | 5.13 | 80 |
| 17.7 | 5.01 | sh |
| 18.7** | 4.75 | 1 |
| 20.9 | 4.25 | 54 |
| 21.9* | 4.06 | 100 |
| 22.7** | 3.917 | sh |
| 23.25 | 3.826 | 27 |
| 24.9 | 3.576 | 6 |
| 25.8 | 3.453 | 1 |
| 26.85* | 3.320 | 16 |
| 27.1 | 3.290 | sh |
| 28.3 | 3.153 | 44 |
| 29.0 | 3.079 | 10 |
| 31.45* | 2.844 | sh |
| 32.1 | 2.788 | 37 |
| 32.4* | 2.763 | sh |
| 34.3* | 2.614 | 7 |
| 35.2** | 2.550 | 1 |
| 35.8 | 2.508 | 2 |
| 37.6* | 2.392 | 2 |
| 39.4 | 2.287 | 1 |
| 40.9 | 2.206 | 1 |
| 41.8 | 2.161 | 4 |
| 42.5 | 2.127 | 5 |
| 44.5 | 2.036 | 4 |
| 47.5 | 1.914 | 2 |
| 48.3* | 1.884 | 4 |
| 48.8 | 1.866 | 4 |
| 49.4 | 1.845 | 5 |
| 51.0 | 1.791 | 7 |
| 55.2 | 1.664 | 4 |

*peak may contain impurity
**impurity (b) A portion of the as-synthesized MgAPSO-35 of part (a) was calcined in air at 500° C. for about 68 hours. The calcined powder was characterized by the x-ray powder diffraction pattern below:

| 2θ | d, (Å) | 100 × I/Io |
|---|---|---|
| 8.5 | 10.40 | 21 |
| 10.8 | 8.19 | 100 |
| 11.3* | 7.83 | sh |
| 13.3 | 6.66 | 76 |
| 15.8 | 5.61 | 3 |
| 17.2 | 5.16 | 31 |
| 20.15* | 4.41 | 110 |
| 20.8 | 4.27 | sh |
| 21.25* | 4.18 | 97 |
| 21.85 | 4.07 | 40 |
| 22.8* | 3.900 | 43 |
| 23.1 | 3.850 | sh |
| 24.2* | 3.678 | 6 |
| 24.8 | 3.590 | 6 |
| 26.2* | 3.401 | 45 |
| 27.0 | 3.302 | 10 |
| 27.3 | 3.267 | 10 |

-continued

| 2θ | d, (Å) | 100 × I/Io |
|---|---|---|
| 28.3 | 3.153 | 24 |
| 29.5 | 3.028 | 19 |
| 30.9* | 2.894 | 5 |
| 31.4 | 2.849 | 7 |
| 32.2 | 2.780 | 19 |
| 32.7 | 2.739 | sh |
| 33.8* | 2.652 | 4 |
| 34.4 | 2.607 | 5 |
| 35.3* | 2.543 | 21 |
| 36.0 | 2.495 | 4 |
| 37.2* | 2.417 | 4 |
| 38.4 | 2.344 | 6 |
| 39.8 | 2.265 | 4 |
| 40.9 | 2.206 | 2 |
| 41.9 | 2.156 | 5 |
| 42.6 | 2.122 | 6 |
| 43.5* | 2.085 | 3 |
| 44.8 | 2.023 | 2 |
| 45.1 | 2.010 | 4 |
| 48.4 | 1.881 | 2 |
| 49.3 | 1.848 | 2 |
| 51.3 | 1.781 | 3 |
| 55.5 | 1.656 | 5 |

*impurity peak (c) The MgAPSO-35 compositions are generally characterized by the data of Table XIX below:

TABLE XIX

| 2θ | d, (Å) | Relative Intensity |
|---|---|---|
| 10.6–11.1 | 8.35–7.97 | m–vs |
| 13.1–13.7 | 6.76–6.46 | w–vs |
| 17.0–17.6 | 5.22–5.04 | m–s |
| 20.6–21.2 | 4.31–4.19 | vw–m |
| 21.6–22.2 | 4.11–4.00 | m–vs |
| 28.1–28.8 | 3.175–3.100 | m |

(d) The MgAPSO-35 compositions for which x-ray powder diffraction data have been obtained to date have patterns which are characterized by the x-ray powder diffraction pattern shown in Table XX, below:

TABLE XX

| 2θ | d, (Å) | 100 × I/Io |
|---|---|---|
| 8.3–8.8 | 10.65–10.05 | 10–21 |
| 10.6–11.1 | 8.35–7.97 | 36–100 |
| 13.1–13.7 | 6.76–6.46 | 17–100 |
| 15.7–16.0 | 5.64–5.54 | 0–9 |
| 17.0–17.6 | 5.22–5.04 | 25–80 |
| 17.7–17.8 | 5.01–4.98 | 0–sh |
| 20.6–21.2 | 4.31–4.19 | sh–54 |
| 21.6–22.2 | 4.11–4.00 | 40–100 |
| 23.0–23.7 | 3.867–3.754 | sh–27 |
| 24.6–25.2 | 3.619–3.534 | 5–8 |
| 25.8–26.4 | 3.453–3.376 | 0–8 |
| 26.6–27.3 | 3.351–3.267 | 10–16 |
| 27.1 | 3.290 | sh–10 |
| 28.1–28.8 | 3.175–3.100 | 24–44 |
| 28.9–29.7 | 3.089–3.008 | 5–23 |
| 31.45–31.5 | 2.844–2.840 | sh–7 |
| 31.9–32.4 | 2.805–2.763 | 19–37 |
| 32.4–32.7 | 2.763–2.739 | sh |
| 34.1–34.7 | 2.629–2.585 | 5–9 |
| 35.6–36.1 | 2.522–2.488 | 0–4 |
| 37.1–38.0 | 2.404–2.368 | 0–6 |
| 39.4–39.9 | 2.287–2.259 | 0–4 |
| 40.8–40.9 | 2.212–2.206 | 0–1 |
| 41.7–42.2 | 2.166–2.141 | 0–5 |
| 42.2–42.7 | 2.132–2.118 | 0–6 |
| 44.5–44.8 | 2.036–2.023 | 0–7 |
| 45.0–45.1 | 2.014–2.010 | 0–1 |
| 47.4–47.7 | 1.914–1.907 | 0–2 |
| 48.2–48.6 | 1.888–1.873 | 0–4 |
| 48.7–49.0 | 1.870–1.859 | 0–4 |
| 49.3–49.7 | 1.848–1.834 | 0–5 |
| 50.8–51.5 | 1.797–1.774 | 0–7 |
| 55.2–55.6 | 1.664–1.653 | 0–4 |

EXAMPLE 116

(a) MgAPSO-36, as prepared in example 5, was subjected to x-ray analysis. MgAPSO-36 was determined to have a characteristic x-ray powder diffraction pattern which contains the d-spacings set forth below:

| 2θ | d, (Å) | 100 × I/Io |
|---|---|---|
| 7.4** | 11.95 | sh |
| 7.9 | 11.19 | 100 |
| 8.1 | 10.92 | sh |
| 12.8** | 6.92 | 3 |
| 13.45 | 6.58 | 6 |
| 14.75** | 6.01 | 4 |
| 15.7 | 5.64 | (sh) |
| 16.3 | 5.44 | 31 |
| 18.9 | 4.70 | 41 |
| 19.5** | 4.55 | 7 |
| 20.7* | 4.29 | 49 |
| 21.55 | 4.12 | (sh) |
| 21.8 | 4.077 | (sh) |
| 22.35* | 3.978 | 42 |
| 22.8 | 3.900 | (sh) |
| 23.8 | 3.739 | 9 |
| 25.7** | 3.466 | 6 |
| 27.1 | 3.290 | 14 |
| 28.2 | 3.164 | 10 |
| 28.9* | 3.089 | 12 |
| 30.1 | 2.969 | 7 |
| 31.8 | 2.814 | 11 |
| 33.0* | 2.714 | 3 |
| 34.6* | 2.592 | 16 |
| 35.7 | 2.515 | 4 |
| 37.6* | 2.349 | 3 |
| 39.3 | 2.293 | 1 |
| 40.1 | 2.249 | 3 |
| 41.3 | 2.186 | 4 |
| 42.0** | 2.151 | 2 |
| 43.0 | 2.103 | 2 |
| 44.0 | 2.058 | 2 |
| 45.3 | 2.002 | 1 |
| 46.6 | 1.949 | 1 |
| 47.3 | 1.922 | 3 |
| 48.8 | 1.867 | 1 |
| 51.1 | 1.787 | 2 |
| 53.7 | 1.707 | 2 |
| 55.4 | 1.659 | 3 |

*peak may contain impurity
**impurity peak

| 2θ | d, (Å) | 100 × I/Io |
|---|---|---|
| 7.4** | 11.95 | sh |
| 7.9 | 11.19 | 100 |
| 8.2 | 10.78 | sh |
| 12.8** | 6.92 | 3 |
| 13.45 | 6.58 | 8 |
| 14.9** | 5.95 | 2 |
| 15.9 | 5.57 | sh |
| 16.5 | 5.37 | 24 |
| 19.3 | 4.60 | 38 |
| 19.75** | 4.50 | sh |
| 20.8 | 4.27 | 25 |
| 21.2** | 4.19 | sh |
| 21.8 | 4.08 | sh |
| 22.35 | 3.978 | 25 |
| 22.6** | 3.934 | sh |
| 23.0 | 3.867 | sh |
| 23.9 | 3.723 | 5 |
| 24.9** | 3.576 | 1 |
| 25.8** | 3.453 | 4 |

-continued

| 2θ | d,(Å) | 100 × I/Io |
|---|---|---|
| 27.2 | 3.278 | 16 |
| 28.35 | 3.148 | 7 |
| 29.1* | 3.069 | 10 |
| 29.9 | 2.988 | 3 |
| 30.4* | 2.940 | 5 |
| 32.0 | 2.797 | 8 |
| 33.2 | 2.698 | 1 |
| 35.0* | 2.564 | 7 |
| 36.0 | 2.495 | 3 |
| 37.7* | 2.386 | 2 |
| 39.5 | 2.281 | 1 |
| 40.3 | 2.238 | 2 |
| 41.3 | 2.186 | 4 |
| 42.0** | 2.151 | 2 |
| 43.5 | 2.080 | 1 |
| 44.3 | 2.045 | 1 |
| 45.4 | 1.998 | 1 |
| 47.6 | 1.910 | 3 |
| 51.2 | 1.784 | 1 |
| 55.5 | 1.656 | 1 |

*peak may contain impurity
**impurity peak (c) The MgAPSO-36 compositions are generally characterized by the data of Table XXI below:

TABLE XXI

| 2θ | d, (Å) | Relative Intensity |
|---|---|---|
| 7.8–8.0 | 11.33–11.05 | vs |
| 16.3–16.5 | 5.44–5.37 | m |
| 18.9–19.3 | 4.70–4.60 | m |
| 20.7–20.8 | 4.29–4.27 | m |
| 22.35 | 3.98 | m |

(d) The MgAPSO-36 compositions for which x-ray powder diffraction data have been obtained to date have patterns which are characterized by the x-ray powder diffraction pattern shown in Table XXII below:

TABLE XXII

| 2θ | d, (Å) | 100 × I/Io |
|---|---|---|
| 7.8–8.0 | 11.33–11.05 | 100 |
| 8.1–8.2 | 10.92–10.78 | 0–sh |
| 13.45 | 6.58 | 6–8 |
| 15.7–15.9 | 5.64–5.57 | sh |
| 16.3–16.5 | 5.44–5.37 | 24–31 |
| 18.9–19.3 | 4.70–4.60 | 38–41 |
| 20.7–20.8 | 4.29–4.27 | 25–49 |
| 21.0 | 4.23 | 0–sh |
| 21.55–21.8 | 4.12–4.08 | sh |
| 21.8–21.9 | 4.077–4.058 | sh |
| 22.35 | 3.978 | 25–42 |
| 22.8–23.0 | 3.900–3.867 | (sh) |
| 23.8–23.9 | 3.739–3.723 | 5–9 |
| 27.1–27.2 | 3.290–3.278 | 14–16 |
| 28.1–28.35 | 3.176–3.148 | 7–10 |
| 28.8–29.1 | 3.100–3.069 | 10–12 |
| 29.9–30.1 | 2.988–2.969 | 3–7 |
| 31.8–32.0 | 2.814–2.797 | 8–11 |
| 33.0–33.2 | 2.714–2.698 | 1–3 |
| 34.6–35.0 | 2.592–2.564 | 7–16 |
| 35.7–36.0 | 2.515–2.495 | 3–4 |
| 37.6–37.7 | 2.392–2.386 | 2–3 |
| 39.3–39.5 | 2.293–2.281 | 1 |
| 40.1–40.3 | 2.249–2.238 | 2–3 |
| 41.3 | 2.186 | 4 |
| 43.0–43.5 | 2.103–2.080 | 1–2 |
| 43.95–44.3 | 2.060–2.045 | 1–2 |
| 45.2–45.4 | 2.006–1.998 | 1 |
| 46.6 | 1.949 | 0–1 |
| 47.3–47.6 | 1.922–1.910 | 3 |
| 48.8 | 1.867 | 0–1 |
| 51.1–51.2 | 1.787–1.784 | 1–2 |
| 53.7 | 1.707 | 0–2 |

TABLE XXII-continued

| 2θ | d, (Å) | 100 × I/Io |
|---|---|---|
| 55.3–55.5 | 1.661–1.656 | 1–3 |

EXAMPLE 117

(a) MgAPSO-39, as prepared in example 55, was subjected to x-ray analysis. MgAPSO-39 was determined to have a characteristic x-ray powder diffraction pattern which contains at least the d-spacings set forth below:

| 2θ | d, (Å) | 100 × I/Io |
|---|---|---|
| 8.1** | 10.92 | 6 |
| 8.5** | 10.40 | 15 |
| 8.9** | 9.98 | 1 |
| 9.45* | 9.34 | 30 |
| 12.4** | 7.13 | 2 |
| 13.4* | 6.60 | 48 |
| 14.2** | 6.22 | 2 |
| 14.4** | 6.15 | 2 |
| 14.6** | 6.06 | 2 |
| 15.65** | 5.66 | 4 |
| 18.15 | 4.89 | 33 |
| 20.3** | 4.38 | 17 |
| 21.3* | 4.18 | 70 |
| 22.1** | 4.027 | 13 |
| 22.6* | 3.929 | 100 |
| 23.15** | 3.844 | 10 |
| 26.4** | 3.375 | 3 |
| 27.0 | 3.301 | 4 |
| 27.8** | 3.208 | 3 |
| 28.0* | 3.191 | 4 |
| 28.7* | 3.113 | 9 |
| 29.7 | 3.007 | 13 |
| 30.3 | 2.953 | 25 |
| 31.7** | 2.823 | 5 |
| 32.7 | 2.736 | 12 |
| 34.1* | 2.632 | 7 |
| 35.1** | 2.555 | 2 |
| 36.7* | 2.448 | 2 |
| 38.1* | 2.361 | 9 |
| 39.25** | 2.295 | 2 |
| 41.0 | 2.200 | 2 |
| 43.3 | 2.089 | 2 |
| 43.8 | 2.067 | 1 |
| 45.0 | 2.015 | 1 |
| 46.2* | 1.966 | 2 |
| 47.2* | 1.926 | 1 |
| 48.8 | 1.867 | 4 |
| 49.4 | 1.845 | 3 |
| 51.45* | 1.776 | 4 |
| 52.3 | 1.749 | 2 |
| 54.55 | 1.683 | 2 |

*peak may contain impurity
**impurity peak (b) The MgAPSO-39 compositions are generally characterized by the data of Table XXIII below:

TABLE XXIII

| 2θ | d, (Å) | Relative Intensity |
|---|---|---|
| 9.2–9.6 | 9.61–9.21 | m |
| 13.1–13.5 | 6.76–6.56 | m |
| 17.8–18.3 | 4.98–4.85 | m |
| 20.8–21.3 | 4.27–4.17 | m–vs |
| 22.2–22.8 | 4.00–3.90 | vs |
| 30.0–30.3 | 2.979–2.950 | w–m |

(c) The MgAPSO-39 compositions for which x-ray powder diffraction data have been obtained to date have patterns which are characterized by the x-ray powder diffraction pattern shown in Table XXIV below.

TABLE XXIV

| 2θ | d, (Å) | 100 × I/Io |
|---|---|---|
| 9.2–9.6 | 9.61–9.21 | 20–53 |
| 13.1–13.5 | 6.76–6.56 | 25–53 |
| 17.8–18.3 | 4.98–4.85 | 23–34 |
| 20.8–21.3 | 4.27–4.17 | 70–100 |
| 22.2–22.8 | 4.004–3.900 | 97–100 |
| 26.8–27.05 | 3.326–3.296 | 3–4 |
| 28.0–28.2 | 3.191–3.175 | 0–4 |
| 28.6–28.8 | 3.121–3.100 | sh–17 |
| 29.4–29.8 | 3.038–2.998 | 13–20 |
| 30.0–30.3 | 2.979–2.950 | 17–29 |
| 32.4–32.8 | 2.763–2.730 | 10–16 |
| 33.9–34.2 | 2.644–2.622 | sh–11 |
| 36.7–36.85 | 2.448–2.439 | 0–2 |
| 37.8–38.1 | 2.380–2.362 | 5–9 |
| 40.7–41.0 | 2.217–2.201 | 0–5 |
| 43.0–43.4 | 2.103–2.085 | 0–2 |
| 45.0 | 2.014 | 0–1 |
| 46.2–46.3 | 1.966–1.961 | 0–2 |
| 47.2–47.3 | 1.926–1.922 | 0–1 |
| 48.5–48.85 | 1.877–1.864 | 4–5 |
| 49.0–49.5 | 1.859–1.841 | 0–3 |
| 51.0–51.5 | 1.791–1.778 | 3–5 |
| 52.1–52.4 | 1.755–1.746 | 0–4 |
| 54.2–54.6 | 1.692–1.681 | 0–2 |

EXAMPLE 118

(a) MgAPSO-43, as prepared in example 92, was subjected to x-ray analysis. MgAPSO-43 was determined to have a characteristic x-ray powder diffraction pattern which contains the d-spacings set forth below:

| 2θ | d, (Å) | 100 × I/Io |
|---|---|---|
| 6.5** | 13.63 | 8 |
| 7.6** | 11.66 | 35 |
| 12.3 | 7.20 | 100 |
| 13.05** | 6.77 | 4 |
| 14.45** | 6.14 | 4 |
| 15.15* | 5.85 | 2 |
| 16.5** | 5.37 | 3 |
| 17.3 | 5.13 | 12 |
| 19.7* | 4.51 | 3 |
| 20.35** | 4.37 | 2 |
| 21.45* | 4.14 | 49 |
| 22.65** | 3.928 | 6 |
| 23.9** | 3.726 | 3 |
| 24.0 | 3.701 | 3 |
| 24.35 | 3.653 | 2 |
| 26.7* | 3.336 | 7 |
| 27.6 | 3.232 | 39 |
| 28.05* | 3.182 | 18 |
| 28.55* | 3.126 | 5 |
| 29.65** | 2.013 | 1 |
| 30.95** | 2.889 | 2 |
| 32.8** | 2.729 | 7 |
| 33.05 | 2.710 | 8 |
| 35.8* | 2.510 | 3 |
| 38.3** | 2.350 | 2 |
| 39.55** | 2.278 | 1 |
| 43.75** | 2.070 | 2 |
| 44.05** | 2.055 | 1 |
| 45.4 | 1.997 | 3 |
| 45.65** | 1.998 | 3 |
| 49.0** | 1.859 | 3 |
| 51.1* | 1.788 | 4 |
| 52.0* | 1.759 | 1 |
| 53.0 | 1.728 | 3 |
| 53.7 | 1.707 | 2 |

*peak may contain impurity
**impurity peak (b) A portion of the as-synthesized MgAPSO-43 of part (a) was calcined in air at 500° C. for about 1 hour and at 600° C. for about 1.5 hours. The calcined product was characterized by the x-ray powder diffraction pattern below:

| 2θ | d, (Å) | 100 × I/Io |
|---|---|---|
| 6.95* | 12.73 | 30 |
| 8.15* | 10.87 | 47 |
| 12.95 | 6.83 | 35 |
| 17.4 | 5.10 | 10 |
| 21.45 | 4.14 | 100 |
| 23.2* | 3.832 | 44 |
| 28.15 | 3.167 | 25 |

*impurity peak (c) The MgAPSO-43 compositions are generally characterized by the data of Table XXV below:

TABLE XXV

| 2θ | d, (Å) | Relative Intensity |
|---|---|---|
| 12.3–12.95 | 7.20–6.83 | m–vs |
| 17.3–17.45 | 5.13–5.09 | w |
| 21.45–21.6 | 4.15–4.12 | m–vs |
| 27.6–27.75 | 3.232–3.215 | m |
| 33.05–33.2 | 2.710–2.699 | w |

(d) The MgAPSO-43 compositions for which x-ray powder diffraction data have been obtained to date have patterns which are characterized by the x-ray powder diffraction pattern shown in Table XXVI below:

TABLE XXVI

| 2θ | d, (Å) | 100 × I/Io |
|---|---|---|
| 12.3–12.95 | 7.20–6.83 | 35–100 |
| 15.15–15.5 | 5.85–5.37 | 2–4 |
| 17.3–17.45 | 5.13–5.09 | 12 |
| 19.7–19.85 | 4.51–4.47 | 3–5 |
| 21.45–21.6 | 4.15–4.12 | 49–100 |
| 24.35–24.5 | 3.653–3.635 | 2 |
| 26.7–26.85 | 3.336–3.319 | 7–9 |
| 27.6–27.75 | 3.232–3.215 | 39–50 |
| 28.05–28.2 | 3.182–3.165 | 18–25 |
| 28.55–28.75 | 3.126–3.107 | 5–6 |
| 33.05–33.2 | 2.710–2.699 | 8–12 |
| 35.8–35.9 | 2.510–2.502 | 3–4 |
| 45.4–45.55 | 1.997–1.991 | 3 |
| 51.1–51.2 | 1.788–1.785 | 4 |
| 52.0–52.25 | 1.759–1.750 | 1–2 |
| 53.0–53.1 | 1.728–1.725 | 3–4 |
| 53.7–53.95 | 1.707–1.700 | 2 |

EXAMPLE 119

(a) MgAPSO-44, as prepared in example 88, was subjected to x-ray analysis. MgAPSO-44 was determined to have a characteristic x-ray powder diffraction pattern which contains the d-spacings set forth below:

| 2θ | d, (Å) | 100 × I/Io |
|---|---|---|
| 6.7** | 13.19 | 64 |
| 7.3** | 12.11 | 12 |
| 9.35 | 9.46 | 100 |
| 12.95* | 6.84 | 16 |
| 13.7 | 6.46 | 2 |
| 14.5 | 6.11 | 5 |
| 14.8** | 5.99 | 3 |
| 16.1 | 5.54 | 35 |
| 17.3 | 5.13 | 7 |
| 18.9 | 4.70 | 8 |
| 19.6** | 4.53 | 9 |
| 20.7 | 4.29 | 100 |
| 20.9** | 4.25 | sh |
| 21.7 | 4.10 | 13 |
| 22.3** | 3.986 | 28 |
| 22.5 | 3.952 | sh |

-continued

| 2θ | d, (Å) | 100 × I/Io |
|---|---|---|
| 23.0 | 3.867 | 7 |
| 24.3 | 3.663 | 37 |
| 25.8** | 3.453 | sh |
| 26.1 | 3.414 | 7 |
| 27.5 | 3.243 | 10 |
| 28.8** | 3.998 | 4 |
| 29.6 | 3.018 | sh |
| 29.9* | 2.988 | 15 |
| 30.7 | 2.912 | 48 |
| 31.4 | 2.849 | 1 |
| 32.4 | 2.763 | 4 |
| 32.7 | 2.739 | 3 |
| 33.4** | 2.683 | 1 |
| 34.3** | 2.614 | 3 |
| 34.8 | 2.578 | 4 |
| 35.4 | 2.536 | 6 |
| 36.8 | 2.442 | 1 |
| 37.5** | 2.398 | 3 |
| 38.4 | 2.344 | 1 |
| 39.1 | 2.304 | 1 |
| 39.8 | 2.265 | 1 |
| 42.0* | 2.146 | 6 |
| 43.4 | 2.085 | 2 |
| 46.5 | 1.957 | 1 |
| 47.1 | 1.929 | 3 |
| 48.0* | 1.895 | 8 |
| 48.5 | 1.877 | 5 |
| 50.1 | 1.821 | 10 |
| 51.8 | 1.768 | 1 |
| 53.6 | 1.710 | 10 |
| 54.6 | 1.681 | 1 |
| 55.3** | 1.661 | 1 |

*peak may contain impurity
**impurity peak (b) A portion of the as-synthesized MgAPSO-44 of part (a) was calcined in air for 2.5 hours at 500° C. and then for 0.25 hour at 600° C. The calcined product was characterized by the x-ray powder diffraction pattern below:

| 2θ | d, (Å) | 100 × I/Io |
|---|---|---|
| 2.9** | 30.46 | 8 |
| 7.35** | 12.03 | 64 |
| 8.9** | 9.94 | sh |
| 9.1** | 9.72 | sh |
| 9.5 | 9.31 | 100 |
| 12.8* | 6.92 | 35 |
| 13.9 | 6.37 | 4 |
| 14.7** | 6.07 | 3 |
| 16.0 | 5.54 | 20 |
| 17.8 | 4.98 | 53 |
| 19.6** | 4.53 | 14 |
| 20.6 | 4.31 | 82 |
| 21.1** | 4.21 | 16 |
| 22.3* | 3.986 | sh–28 |
| 23.0 | 3.867 | 7–8 |
| 25.0* | 3.562 | 18 |
| 25.8* | 3.453 | 17 |
| 27.6 | 3.232 | 1 |
| 28.2 | 3.164 | 3 |
| 28.9** | 3.089 | 4 |
| 29.8 | 2.998 | 4 |
| 30.5* | 2.931 | 24 |
| 31.0 | 2.885 | 16 |
| 31.6 | 2.831 | sh |
| 32.2 | 2.780 | 1 |
| 33.2 | 2.698 | sh |
| 33.5** | 2.675 | 3 |
| 34.3** | 2.614 | 8 |
| 34.8 | 2.578 | 1 |
| 36.0 | 2.494 | 3 |
| 37.7** | 2.386 | 2 |
| 38.5 | 2.338 | 1 |
| 39.0 | 2.309 | 1 |
| 39.6 | 2.276 | 3 |
| 42.0* | 2.151 | 1 |

-continued

| 2θ | d, (Å) | 100 × I/Io |
|---|---|---|
| 42.9** | 2.108 | 2 |
| 43.3 | 2.090 | 1 |
| 47.5* | 1.918 | 4 |
| 48.8 | 1.866 | 3 |
| 50.8 | 1.797 | 4 |
| 51.6 | 1.771 | 1 |
| 53.0 | 1.728 | 4 |
| 54.3** | 1.689 | 1 |
| 55.6 | 1.656 | 1 |

*peak may contain impurity
**impurity peak (c) The MgAPSO-44 compositions are generally characterized by the data of Table XXVII below:

TABLE XXVII

| 2θ | d, (Å) | 100 × I/Io |
|---|---|---|
| 9.2–9.45 | 9.61–9.37 | vs |
| 15.9–16.1 | 5.57–5.50 | m |
| 17.2–18.0 | 5.16–4.93 | vw–m |
| 20.5–20.75 | 4.33–4.28 | m–vs |
| 24.3–25.0 | 3.663–3.562 | w–m |
| 30.5–31.0 | 2.931–2.885 | w–m |

(d) the MgAPSO-44 compositions for which x-ray powder diffraction data have been obtained to date have patterns which are characterized by the x-ray powder diffraction shown in Table XXVIII below:

TABLE XXVIII

| 2θ | d, (Å) | 100 × I/Io |
|---|---|---|
| 9.2–9.45 | 9.61–9.37 | 100 |
| 12.8–13.0* | 6.92–6.81 | 11–35 |
| 13.6–14.0 | 6.51–6.33 | 2–4 |
| 14.5–14.6 | 6.11–6.07 | 0–5 |
| 15.9–16.1 | 5.57–5.50 | 20–36 |
| 17.2–18.0 | 5.16–4.93 | 7 |
| 18.8–19.0 | 4.72–4.67 | 7–53 |
| 20.5–20.75 | 4.33–4.28 | 58–100 |
| 21.7–21.8 | 4.10–4.08 | 0–18 |
| 22.3–22.6 | 3.986–3.934 | sh |
| 23.0–23.3 | 3.867–3.817 | 8 |
| 24.3–25.0* | 3.663–3.562 | 17–58 |
| 25.8–26.15* | 3.453–3.406 | 10–18 |
| 27.5–27.8 | 3.243–3.209 | 1–12 |
| 28.2 | 3.175 | 0–3 |
| 29.6–29.8 | 3.018–2.998 | 0–sh |
| 29.7–30.5* | 3.008–2.931 | 4–15 |
| 30.5–31.0 | 2.931–2.885 | 16–48 |
| 31.4–31.6 | 2.849–2.831 | sh–1 |
| 32.2–32.5 | 2.780–2.755 | 1–5 |
| 32.7–33.2 | 2.739–2.698 | sh–3 |
| 34.8 | 3.578 | 0–1 |
| 35.3–36.0 | 2.543–2.495 | 3–6 |
| 36.8 | 2.442 | 0–1 |
| 38.4–38.6 | 2.344–2.338 | 0–1 |
| 39.0–39.1 | 2.309–2.304 | 0–1 |
| 39.6–40.0 | 2.276–2.254 | 0–1 |
| 42.0–42.2* | 2.151–2.141 | 0–6 |
| 43.3–43.6 | 2.090–2.076 | 0–2 |
| 46.5 | 1.953 | 0–1 |
| 47.1–47.5 | 1.929–1.914 | 0–5 |
| 48.0–48.2* | 1.895–1.888 | 0–8 |
| 48.5–48.8 | 1.877–1.866 | 0–5 |
| 50.0–50.8 | 1.824–1.797 | 4–10 |
| 51.6–51.8 | 1.771–1.765 | 0–1 |
| 53.0–53.8 | 1.728–1.704 | 4–10 |
| 54.3–54.6 | 1.689–1.681 | 0–2 |

*peak may contain impurity

EXAMPLE 120

(a) MgAPSO-46, as prepared in example 44, was subjected to x-ray analysis. MgAPSO-46 was determined to have a characteristic x-ray powder diffraction pattern which contains the d-spacings set forth below:

| 2θ | d, (Å) | 100 × I/Io |
|---|---|---|
| 6.6 | 13.44 | 3 |
| 7.7 | 11.48 | 100 |
| 10.1 | 8.76 | <1 |
| 12.4 | 7.15 | 2 |
| 13.2 | 6.71 | 2 |
| 13.75 | 6.44 | 3 |
| 14.9 | 5.95 | 1 |
| 15.3 | 5.79 | 2 |
| 16.6 | 5.33 | 3 |
| 17.4 | 5.10 | <1 |
| 19.8 | 4.48 | 1 |
| 20.45 | 4.34 | 4 |
| 20.7 | 4.29 | sh |
| 21.5 | 4.13 | 12 |
| 22.75 | 3.906 | 6 |
| 24.2 | 3.682 | 3 |
| 25.2 | 3.534 | <1 |
| 26.85 | 3.320 | 4 |
| 27.7 | 3.219 | 3 |
| 28.2 | 3.163 | 2 |
| 28.7 | 3.109 | 4 |
| 29.8 | 3.000 | 1 |
| 31.1 | 2.873 | 2 |
| 31.7 | 2.823 | <1 |
| 32.9 | 2.722 | <1 |
| 34.2 | 2.622 | 1 |
| 35.85 | 2.505 | 2 |
| 36.5 | 2.462 | <1 |
| 37.2 | 2.417 | <1 |
| 38.4 | 2.344 | <1 |
| 39.6 | 2.276 | <1 |
| 41.0 | 2.201 | <1 |
| 42.2 | 2.141 | <1 |
| 43.9 | 2.062 | 1 |
| 45.9 | 1.977 | <1 |
| 47.5 | 1.914 | <1 |
| 49.4 | 1.845 | <1 |
| 50.1 | 1.821 | <1 |
| 51.4 | 1.778 | <1 |
| 52.2 | 1.752 | <1 |

(b) A portion of the as-synthesized MgAPSO-46 of part (a) was calcined in nitrogen at 500° C. for about 1.75 hours. The calcined product was characterized by the x-ray powder diffraction pattern below:

| 2θ | d, (Å) | 100 × I/Io |
|---|---|---|
| 6.8 | 13.0 | 8 |
| 7.8 | 11.33 | 100 |
| 13.5 | 6.56 | 8 |
| 14.0 | 6.33 | 3 |
| 15.2 | 5.83 | 9 |
| 15.6 | 5.68 | sh |
| 16.95 | 5.23 | 11 |
| 20.2 | 4.40 | sh |
| 20.7 | 4.29 | 6 |
| 21.7 | 4.10 | 10 |
| 23.0 | 3.867 | 6 |
| 24.4 | 3.648 | 3 |
| 27.2 | 3.278 | 4 |
| 27.9 | 3.198 | 3 |
| 28.4 | 3.143 | sh |
| 28.9 | 3.089 | 6 |
| 30.2 | 2.959 | 2 |
| 31.4 | 2.849 | 3 |
| 32.0 | 2.797 | 1 |
| 33.4 | 2.683 | 2 |
| 34.2 | 2.622 | 2 |
| 36.2 | 2.481 | 2 |
| 37.0 | 2.430 | <1 |
| 40.2 | 2.243 | <1 |
| 41.3 | 2.186 | 1 |
| 44.2 | 2.049 | 1 |
| 46.3 | 1.961 | <1 |
| 47.9 | 1.899 | <1 |
| 50.5 | 1.807 | 1 |
| 51.9 | 1.762 | <1 |
| 52.6 | 1.740 | <1 |

(c) The MgAPSO-46 compositions are generally characterized by the data of Table XXIX below:

TABLE XXIX

| 2θ | d, (Å) | Relative Intensity |
|---|---|---|
| 7.2–8.1 | 12.28–10.92 | vs |
| 21.2–21.8 | 4.19–4.08 | w–m |
| 22.5–23.0 | 3.952–3.867 | vw–m |
| 26.6–27.2 | 3.351–3.278 | vw–w |
| 28.5–29.0 | 3.132–3.079 | vw–w |

(d) The MgAPSO-46 compositions for which x-ray powder diffraction data have been obtained to date have patterns which are characterized by the x-ray powder diffraction pattern shown in Table XXX below:

TABLE XXX

| 2θ | d, (Å) | 100 × I/Io |
|---|---|---|
| 6.5–6.9 | 13.60–12.81 | 3–10 |
| 7.2–8.1 | 12.28–10.92 | 100 |
| 9.8–10.3 | 9.03–8.59 | 0–1 |
| 12.4 | 7.14 | 0–4 |
| 12.9–13.5 | 6.86–6.56 | 2–8 |
| 13.5–14.0 | 6.56–6.33 | 3–8 |
| 14.8–15.2 | 5.99–5.83 | 1–9 |
| 15.2–15.8 | 5.83–5.61 | (sh)–5 |
| 16.5–17.6 | 5.37–5.04 | 3–11 |
| 17.3–17.4 | 5.13–5.10 | 0–1 |
| 19.7–20.2 | 4.51–4.40 | (sh)–5 |
| 20.3–20.7 | 4.37–4.29 | 4–9 |
| 21.2–21.8 | 4.19–4.08 | 10–36 |
| 22.5–23.0 | 3.952–3.867 | 6–20 |
| 23.7–24.4 | 3.754–3.648 | 3–11 |
| 25.0–25.5 | 3.562–3.648 | 0–1 |
| 26.6–27.2 | 3.351–3.278 | 4–17 |
| 27.5–27.9 | 3.243–3.198 | 3–12 |
| 28.0–28.4 | 3.255–3.143 | sh–2 |
| 28.5–29.0 | 3.132–3.079 | 4–15 |
| 29.6–30.2 | 3.018–2.959 | 1–4 |
| 30.9–31.4 | 2.894–2.849 | 2–6 |
| 31.6–32.0 | 2.831–2.797 | 1–3 |
| 32.6–33.4 | 2.747–2.683 | 1–2 |
| 33.95–34.4 | 2.640–2.607 | 1–4 |
| 35.7–36.2 | 2.515–2.481 | 2–6 |
| 36.3–37.0 | 2.475–2.430 | 0–2 |
| 37.0–37.6 | 2.430–2.392 | 0–1 |
| 37.9–38.4 | 2.374–2.344 | 0–1 |
| 39.5–40.2 | 2.281–2.243 | 0–1 |
| 40.7–41.3 | 2.217–2.186 | 0–1 |
| 43.7–44.3 | 2.071–2.045 | 0–1 |
| 45.8–46.4 | 1.981–1.957 | 0–1 |
| 47.3–47.9 | 1.922–1.899 | 0–1 |
| 49.2–49.3 | 1.852–1.848 | 0–1 |
| 49.9–50.5 | 1.828–1.807 | 0–1 |
| 51.2–51.9 | 1.784–1.762 | 0–1 |
| 52.1–52.6 | 1.755–1.740 | 0–1 |

EXAMPLE 121

(a) MgAPSO-47, as prepared in example 104, was subjected to x-ray analysis. MgAPSO-47 was determined to have a characteristic x-ray powder diffraction pattern which contains the d-spacings set forth below:

| 2θ | d, (Å) | 100 × I/Io |
|---|---|---|
| 9.5 | 9.29 | 100 |
| 12.95 | 6.84 | 9 |

-continued

| 2θ | d, (Å) | 100 × I/Io |
|---|---|---|
| 13.9 | 6.36 | 5 |
| 16.05 | 5.52 | 22 |
| 17.65 | 5.03 | 9 |
| 19.05 | 4.66 | 2 |
| 20.65 | 4.30 | 53 |
| 21.9 | 4.06 | 7 |
| 22.45* | 3.961 | 2 |
| 23.05 | 3.859 | 7 |
| 24.75 | 3.598 | 21 |
| 25.95 | 3.432 | 12 |
| 27.7 | 3.222 | 5 |
| 27.95 | 3.190 | 3 |
| 28.55* | 3.126 | 1 |
| 29.55 | 3.022 | 3 |
| 30.6 | 2.919 | 21 |
| 30.9 | 2.893 | sh |
| 31.5 | 2.837 | 2 |
| 32.4 | 2.763 | 1 |
| 33.25 | 2.695 | 2 |
| 34.55 | 2.597 | 4 |
| 34.95 | 2.567 | 1 |
| 35.8 | 2.510 | 3 |
| 38.5 | 2.338 | 2 |
| 39.1 | 2.305 | 1 |
| 39.7 | 2.270 | 2 |
| 42.5 | 2.126 | 2 |
| 43.4 | 1.085 | 1 |
| 47.7 | 1.907 | 2 |
| 48.7 | 1.870 | 4 |
| 50.4 | 1.810 | 3 |
| 51.7 | 1.768 | 1 |
| 52.45 | 1.745 | 1 |
| 53.3 | 1.719 | 2 |
| 54.1 | 1.695 | 1 |
| 54.6 | 1.681 | 1 |
| 55.9 | 1.645 | 2 |

*Impurity peak (b) A portion of the as-synthesized MgAPSO-47 of part (a) was calcined in air at 500° C. for about 1.75 hours. The calcined product was characterized by the x-ray powder diffraction pattern below:

| 2θ | d, (Å) | 100 × I/Io |
|---|---|---|
| 9.65 | 9.17 | 100 |
| 13.05 | 6.79 | 20 |
| 14.2 | 6.25 | 4 |
| 16.2 | 5.46 | 14 |
| 18.0 | 4.92 | 11 |
| 19.3 | 4.60 | 3 |
| 20.85 | 4.26 | 33 |
| 22.3 | 3.980 | 2 |
| 22.6* | 3.933 | 3 |
| 23.3 | 3.819 | 4 |
| 23.6* | 3.771 | 1 |
| 24.55* | 3.626 | 2 |
| 25.25 | 3.556 | 12 |
| 26.2 | 3.400 | 10 |
| 28.0 | 3.188 | 2 |
| 28.5 | 3.132 | 4 |
| 29.95 | 2.983 | 2 |
| 30.95 | 2.889 | 15 |
| 31.4 | 2.849 | sh |
| 34.8 | 2.575 | 3 |
| 36.5 | 2.459 | 2 |

*Impurity peak (c) The MgAPSO-47 compositions are generally characterized by the date of Table XXXI below:

TABLE XXXI

| 2θ | d, (Å) | Relative Intensity |
|---|---|---|
| 9.5–9.65 | 9.33–9.17 | vs |
| 12.85–13.05 | 6.89–6.79 | vw–m |
| 16.0–16.2 | 5.54–5.46 | w–m |

TABLE XXXI-continued

| 2θ | d, (Å) | Relative Intensity |
|---|---|---|
| 20.6–20.85 | 4.32–4.26 | m–s |
| 24.75–25.3 | 3.598–3.526 | vw–m |
| 30.55–30.95 | 2.925–2.889 | w–m |

(d) The MgAPSO-47 compositions for which x-ray powder diffraction data have been obtained to date have patterns which are characterized by the x-ray powder diffraction pattern shown in Table XXXII below:

TABLE XXXII

| 2θ | d, (Å) | 100 × I/Io |
|---|---|---|
| 9.5–9.65 | 9.33–9.17 | 100 |
| 12.85–13.05 | 6.89–6.79 | 7–20 |
| 13.9–14.2 | 6.36–6.25 | 3–7 |
| 16.0–16.2 | 5.54–5.46 | 14–41 |
| 17.65–18.0 | 5.03–4.92 | 4–11 |
| 19.0–19.3 | 4.67–4.60 | 2–3 |
| 20.6–20.85 | 4.32–4.26 | 33–89 |
| 21.9–22.3 | 4.06–3.98 | 2–7 |
| 23.0–23.3 | 3.866–3.819 | 3–11 |
| 24.75–25.3 | 3.598–3.526 | 8–22 |
| 25.85–26.2 | 3.444–3.400 | 7–18 |
| 27.6–28.0 | 3.229–3.188 | 2–7 |
| 27.95–28.5 | 3.190–3.132 | 1–4 |
| 29.5–29.95 | 3.030–3.983 | 2–5 |
| 30.55–30.95 | 2.925–2.889 | 13–36 |
| 30.9–31.4 | 2.891–2.849 | sh |
| 31.4–31.5 | 2.849–2.837 | 0–3 |
| 32.4 | 2.763 | 0–1 |
| 33.25 | 2.695 | 0–3 |
| 34.4–34.8 | 2.606–2.575 | 3–7 |
| 34.95 | 2.567 | 0–1 |
| 35.8–36.55 | 2.510–2.459 | 1–4 |
| 38.5 | 2.338 | 0–2 |
| 39.1–39.65 | 2.305–2.273 | 0–4 |
| 39.6–39.7 | 2.275–2.270 | 0–4 |
| 42.5–42.8 | 2.126–2.115 | 0–3 |
| 43.3–43.8 | 2.091–2.067 | 0–2 |
| 47.6–47.7 | 1.911–1.907 | 0–3 |
| 48.7–49.3 | 1.870–1.848 | 1–7 |
| 50.4–51.1 | 1.810–1.787 | 1–5 |
| 51.7 | 1.768 | 0–1 |
| 52.45 | 1.745 | 0–1 |
| 53.3 | 1.719 | 0–2 |
| 54.1 | 1.695 | 0–1 |
| 54.7 | 1.681 | 0–1 |
| 55.99 | 1.645 | 0–2 |

EXAMPLE 122

In order to demonstrate the catalytic activity of the MgAPSO compositions, calcined samples of MgAPSO products were tested for catalytic cracking of n-butane using a bench-scale apparatus.

The reactor was a cylindrical quartz tube 254 mm. in length and 10.3 mm. I.D. In each test the reactor was loaded with particles of the test MgAPSO which were 20–40 mesh (U.S. std.) in size and in an amount of from 0.5 to 5 grams, the quantity being selected so that the conversion of n-butane was at least 5% and not more than 90% under the test conditions. The MgAPSO samples had been previously calcined in air or nitrogen to remove organic materials from the pore system, and were activated in situ in the reactor in a flowing stream of helium at 500° C. for one hour. The feedstock was a helium-n-butane mixture containing 2 mole percent n-butane and was passed through the reactor at a rate of 50 cc./minute. Analysis of the feedstock and the reactor effluent were carried out using conventional gas chromatography techniques. The reactor effluent was analyzed after 10 minutes of on-stream operation.

The pseudo-first order rate constant ($k_A$) was calculated to determine the relative catalytic activity of the MgAPSO compositions. The $k_A$ value (cm$^3$/g min) obtained for the MgAPSO compositions are set forth, below, in Table XXX:

TABLE XXX

| MgAPSO | Prepared in Example No. | Rate Constant ($k_A$)* |
|---|---|---|
| MgAPSO-35 | 80 | 2.6 |
| MgAPSO-34 | 63 | 4.1 |
| MgAPSO-35 | 82 | 0.9 |
| MgAPSO-36 | 5 | 18.0 |
| MgAPSO-46 | 44 | 7.3 |
| MgAPSO-47 | 104 | 1.7 |

*Prior to activation of the MgAPSO samples of the following examples such were calcined as follows:
(a) Example 80: calcined in air at 600° for 2.25 hours;
(b) Example 63: calcined in air at 550° C. for 2 hours;
(c) Example 82: calcined in nitrogen at 425° C. for 2 hours;
(d) Example 5: calcined in air at 500° C. for 2 hours and then at 600° C. for 2 hours;
(e) Example 44: calcined in nitrogen at 500° C. for 1.75 hours; and
(f) Example 104: calcined in air at 500° C. for 1.75 hours.

PROCESS APPLICATIONS

The MgAPSO compositions of the present invention are, in general, hydrophilic and absorb water preferentially over common hydrocarbon molecules such as paraffins, olefins and benzenoid aromatic species, e.g., benzene, xylenes and cumene. Thus, the MgAPSOs as a class are useful as desiccants in such adsorption separation/purification processes as natural gas drying, cracked gas drying. Water is also preferentially adsorbed over the so-called permanent gases such as carbon dioxide, nitrogen, oxygen and hydrogen. These MgAPSOs are therefore suitably employed in the drying of reformer hydrogen streams and in the drying of oxygen, nitrogen or air prior to liquidification.

The present MgAPSO compositions also exhibit novel surface selectivity characteristics which render them useful as catalyst or catalyst bases in a number of hydrocarbon conversion and oxidative combustion reactions. They can be impregnated or otherwise loaded with catalytically active metals by methods well known in the art and used, for example, in fabricating catalyst compositions having silica or alumina bases. Of the general class, those species having pores larger than about 4 Å are preferred for catalytic applications.

Among the hydrocarbon conversion reactions catalyzed by MgAPSO compositions are cracking, hydrocracking, alkylation for both the aromatic and isoparaffin types, isomerization including xylene isomerization, polymerization, reforming, hydrogenation, dehydrogenation, transalkylation, dealkylation, hydrodecyclization and dehydrocyclization.

Using MgAPSO catalyst compositions which contain a hydrogenation promoter such as platinum or palladium, heavy petroleum residual stocks, cyclic stocks and other hydrocrackable charge stocks, can be hydrocracked at temperatures in the range of 400° F. to 825° F. using molar ratios of hydrogen to hydrocarbon in the range of between 2 and 80, pressures between 10 and 3500 p.s.i.g., and a liquid hourly space velocity (LHSV) of from 0.1 to 20, preferably 1.0 to 10.

The MgAPSO catalyst compositions employed in hydrocracking are also suitable for use in reforming processes in which the hydrocarbon feedstocks contact the catalyst at temperatures of from about 700° F. to 1000° F., hydrogen pressures of from 100 to 500 p.s.i.g., LHSV values in the range of 0.1 to 10 hydrogen to hydrocarbon molar ratios in the range of 1 to 20, preferably between 4 and 12.

These same catalysts, i.e. those containing hydrogenation promoters, are also useful in hydroisomerizations processes in which feedstocks such as normal paraffins are converted to saturated branched chain isomers. Hydroisomerization is carried out at a temperature of from about 200° F. to 600° F., preferably 300° F. to 550° F. with an LHSV value of from about 0.2 to 1.0. Hydrogen is supplied to the reactor in admixture with the hydrocarbon feedstock in molar proportions (hydrogen to hydrocarbon) of between 1 and 5.

At somewhat higher temperatures, i.e. from about 650° F. to 1000° F., preferably 850° F. to 950° F. and usually at somewhat lower pressures within the range of about 15 to 50 p.s.i.g., the same catalyst compositions are used to hydroisomerize normal paraffins. Preferably the paraffin feedstock comprises normal paraffins having a carbon number range of $C_7$–$C_{20}$. Contact time between the feedstock and the catalyst is generally relatively short to avoid undesirable side reactions such as olefin polymerization and paraffin cracking. LHSV values in the range of 0.1 to 10, preferably 1.0 to 6.0 are suitable.

The unique crystal structure of the present MgAPSO catalysts and their availability in a form totally void of alkali metal content favor their use in the conversion of alkylaromatic compounds, particularly the catalytic disproportionation of toluene, ethylene, trimethyl benzenes, tetramethyl benzenes and the like. In the disproportionation process, isomerization and transalkylation can also occur. Group VIII noble metal adjuvents alone or in conjunction with Group VI-B metals such as tungsten, molybdenum and chromium are preferably included in the catalyst composition in amounts of from about 3 to 15 weight-% of the overall composition. Extraneous hydrogen can, but need not, be present in the reaction zone which is maintained at a temperature of from about 400° to 750° F., pressures in the range of 100 to 2000 p.s.i.g. and LHSV values in the range of 0.1 to 15.

Catalytic cracking processes are preferably carried out with MgAPSO compositions using feedstocks such as gas oils, heavy naphthas, deasphalted crude oil residua, etc., with gasoline being the principal desired product. Temperature conditions of 850° to 1100° F., LHSV values of 0.5 to 10 pressure conditions of from about 0 to 50 p.s.i.g. are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the MgAPSO catalyst in conjunction with a Group VIII non-noble metal cation such as magnesium and nickel.

In catalytic dealkylation wherein it is desired to cleave paraffinic side chains from aromatic nuclei without substantially hydrogenating the ring structure, relatively high temperatures in the range of about 800°–1000° F. are employed at moderate hydrogen pressures of about 300–1000 p.s.i.g., other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like any of which may contain up to about 5 weight-percent of sulfur and up to about 3 weight-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibited the activity of catalysts of hydrocracking. Consequently, it is necessary to operate at more extreme conditions when it is desired to obtain the same degree of hydrocracking conversion per pass on a relatively nitrogenous feed than are required with a feed containing less organonitrogen compounds. Consequently, the conditions under which denitrogenation, desulfurization and/or hydrocracking can be most expeditiously accomplished in any given situation are necessarily determined in view of the characteristics of the feedstocks in particular the concentration of organonitrogen compounds in the feedstock. As a result of the effect of organonitrogen compounds on the hydrocracking activity of these compositions it is not at all unlikely that the conditions most suitable for denitrogenation of a given feedstock having a relatively high organonitrogen content with minimal hydrocracking, e.g. less than 20 volume percent of fresh feed per pass, might be the same as those preferred for hydrocracking another feedstock having a lower concentration of hydrocracking inhibiting constituents e.g., organonitrogen compounds. Consequently, it has become the practice in this art to establish the conditions under which a certain feed is to be contacted on the basis of preliminary screening tests with the specific catalyst and feedstock.

Isomerization reactions are carried out under conditions similar to those described above for reforming, using somewhat more acidic catalysts. Olefins are preferably isomerized at temperatures of 500°–900° F., while paraffins, naphthenes and alkyl aromatics are isomerized at temperatures of 700°–1000° F. Particularly desirable isomerization reactions contemplated herein include the conversion of n-heptene and/or n-octane to isoheptanes, iso-octanes, butane to iso-butane, methylcyclopentane to cyclohexane, meta-xylene and/or ortho-xylene to paraxylene, 1-butene to 2-butene and/or isobutene, n-hexane to isohexane, cyclohexene to methylcyclopentene etc. The preferred form of the catalyst is a combination of the MgAPSO with polyvalent metal compounds (such as sulfides) of metals of Group II-A, Group II-B and rare earth metals. For alkylation and dealkylation processes the MgAPSO compositions having pores of at least 5 Å are preferred. When employed for dealkylation of alkyl aromatics, the temperature is usually at least 350° F. and ranges up to a temperature at which substantial cracking of the feedstock or conversion products occurs, generally up to about 700° F. The temperature is preferably at least 450° F. and not greater than the critical temperature of the compound undergoing dealkylation. Pressure conditions are applied to retain at least the aromatic feed in the liquid state. For alkylation the temperature can be as low as 250° F. but is preferably at least 350° F. In the alkylation of benzene, toluene and xylene, the preferred alkylating agents are olefins such as ethylene and propylene.

We claim:

1. Process for converting a hydrocarbon which comprises contacting said hydrocarbon under hydrocarbon converting conditions with a molecular sieve, said molecular sieve being a crystalline molecular sieve having three-dimensional microporous framework structures of $MgO_2$, $AlO_2$, $PO_2$ and $SiO_2$ tetrahydral units having an empirical chemical composition on an anhydrous basis expressed by the formula:

$$mR:(Mg_wAl_xP_ySi_z)O_2$$

wherein "R" represents at least one organic templating agent present in the intracrystalline pore system; "m" represents the molar amount of "R" present per mole of $(Mg_wAl_xP_ySi_z)O_2$ and has a value between zero (0) and about 0.3; and "w", "y" and "z" represent the mole fractions of magnesium, aluminum, phosphorus and silicon, respectively, present as tetrahedral oxides, said mole fractions being such that they are within the pentagonal compositional area defined by points A, B, C, D, and E of FIG. 1 and each has a value of at least 0.01.

2. Process according to claim 1 wherein the mole fractions of magnesium, aluminum, phosphorus and silicon present as tetrahedral oxides in said crystalline molecular sieve are within the tetragonal compositional area defined by points a, b, c and d of FIG. 2.

3. Process according to claim 1 wherein the mole fractions "w" and "z" of magnesium and silicon respectively in said crystalline molecular sieve satisfy the following relationships:

$$w \geq 0.04$$

$$z \geq 0.04.$$

4. Process according to claim 1 wherein, before being contacted with said mixture of molecular species, said molecular sieve is calcined at a temperature sufficiently high to remove at least some of any organic templating agent present in the intracrystalline pore system.

5. Process according to claim 1 wherein said crystalline molecular sieve has a characteristic X-ray powder diffraction pattern which contains at least the d-spacings set forth in one of the following Tables A to H and J to N:

TABLE A

| 2θ | (MgAPSO-5) d(Å) | Relative Intensity |
|---|---|---|
| 7.2–7.4 | 12.28–11.95 | m–vs |
| 14.6–14.95 | 6.07–5.93 | w–m |
| 19.4–19.8 | 4.58–4.48 | m |
| 20.85–21.1 | 4.26–4.21 | vw–vs |
| 22.15–22.4 | 4.01–3.97 | m–vs |
| 25.6–25.95 | 3.480–3.434 | m |

TABLE B

| 2Θ | (MgAPSO-11) d(Å) | Relative Intensity |
|---|---|---|
| 9.0–9.6 | 9.83–9.21 | vw–m |
| 20.8–21.2 | 4.27–4.19 | vs |
| 22.0–22.4 | 4.04–3.97 | vw–m |
| 22.4–22.8 | 3.97–3.90 | vw–vs |
| 22.8–23.1 | 3.90–3.85 | m |

TABLE C

| 2Θ | (MgAPSO-16) d(Å) | Relative Intensity |
|---|---|---|
| 11.4–11.5 | 7.76–7.69 | m |
| 18.7–18.8 | 4.75–4.72 | w–m |
| 21.85–22.2 | 4.07–4.00 | vs |
| 22.8–23.3 | 3.900–3.818 | w–m |
| 26.75–27.3 | 3.332–3.267 | w–m |
| 29.7–29.9 | 3.008–2.988 | w–m |

TABLE D

| 2Θ | (MgAPSO-20) d(Å) | Relative Intensity |
|---|---|---|
| 13.8–14.2 | 6.42–6.23 | m–vs |
| 19.6–20.15 | 4.53–4.41 | m |
| 24.1–24.7 | 3.695–3.603 | m–vs |
| 27.9–28.6 | 3.198–3.121 | w |
| 31.3–32.05 | 2.861–2.791 | w |
| 34.35–35.0 | 2.610–2.601 | w |

TABLE E

| 2Θ | (MgAPSO-31) d(Å) | Relative Intensity |
|---|---|---|
| 8.4–9.501 | 10.53–9.3084 | w–s |
| 20.2–20.4 | 4.40–4.35 | m |
| 22.0–22.1 | 4.040–4.022 | m |
| 22.5–22.7 | 3.952–3.92 | vs |
| 31.6–31.8 | 2.831–2.814 | w–m |

TABLE F

| 2Θ | (MgAPSO-34) d(Å) | Relative Intensity |
|---|---|---|
| 9.3–9.7 | 9.51–9.12 | vs |
| 15.8–16.3 | 5.61–5.44 | w–m |
| 20.25–21.0 | 4.39–4.19 | m–vs |
| 25.7–26.3 | 3.466–3.389 | vw–m |
| 30.0–30.8 | 2.979–2.903 | vw–m |
| 30.9–31.4 | 2.894–2.849 | w–m |

TABLE G

| 2Θ | (MgAPSO-35) d(Å) | Relative Intensity |
|---|---|---|
| 10.6–11.1 | 8.35–7.97 | m–vs |
| 13.1–13.7 | 6.76–6.46 | w–vs |
| 17.0–17.6 | 5.22–5.04 | m–s |
| 20.6–21.2 | 4.31–4.19 | vw–m |
| 21.6–22.2 | 4.11–4.00 | m–vs |
| 28.1–28.8 | 3.175–3.100 | m |

TABLE H

| 2Θ | (MgAPSO-36) d(Å) | Relative Intensity |
|---|---|---|
| 7.8–8.0 | 11.33–11.05 | vs |
| 16.3–16.5 | 5.44–5.37 | m |
| 18.9–19.3 | 4.70–4.60 | m |
| 20.7–20.8 | 4.29–4.27 | m |
| 22.35 | 3.981 | m |

TABLE J

| 2Θ | (MgAPSO-39) d(Å) | Relative Intensity |
|---|---|---|
| 9.2–9.6 | 9.61–9.21 | m |
| 13.1–13.5 | 6.76–6.56 | m |
| 17.8–18.3 | 4.98–4.85 | m |
| 20.8–21.3 | 4.27–4.17 | m–vs |
| 22.2–22.8 | 4.00–3.90 | vs |
| 30.0–30.3 | 2.979–2.950 | w–m |

TABLE K

| 2Θ | (MgAPSO-43) d(Å) | Relative Intensity |
|---|---|---|
| 12.3–12.95 | 7.20–6.83 | m–vs |
| 17.3–17.45 | 5.13–5.09 | w |
| 21.45–21.6 | 4.15–4.12 | m–vs |
| 27.6–27.75 | 3.232–3.215 | m |
| 33.05–33.2 | 2.710–2.699 | vw–w |

TABLE L

| 2Θ | (MgAPSO-44) d(Å) | Relative Intensity |
|---|---|---|
| 9.2–9.45 | 9.61–9.37 | vs |
| 15.9–16.1 | 5.57–5.50 | m |
| 17.2–18.0 | 5.16–4.93 | vw–m |
| 20.5–20.75 | 4.33–4.28 | m–vs |
| 24.3–25.0 | 3.663–3.562 | w–m |
| 30.5–31.0 | 2.931–2.885 | w–m |

TABLE M

| 2Θ | (MgAPSO-46) d(Å) | Relative Intensity |
|---|---|---|
| 7.2–8.1 | 12.28–10.92 | vs |
| 21.2–21.8 | 4.19–4.08 | w–m |
| 22.5–23.0 | 3.952–3.867 | vw–w |
| 26.6–27.2 | 3.351–3.278 | vw–w |
| 28.5–29.0 | 3.132–3.079 | vw–w |

TABLE N

| 2Θ | (MgAPSO-47) d(Å) | Relative Intensity |
|---|---|---|
| 9.5–9.65 | 9.33–9.17 | vs |
| 12.85–13.05 | 6.89–6.79 | vw–m |
| 16.0–16.2 | 5.54–5.46 | w–m |
| 20.6–20.85 | 4.32–4.26 | m–s |
| 24.75–25.3 | 3.598–3.526 | vw–m |
| 30.55–30.95 | 2.925–2.889 | w–m. |

* * * * *